(12) United States Patent
Jordan et al.

(10) Patent No.: US 9,604,997 B2
(45) Date of Patent: Mar. 28, 2017

(54) PERI-CARBINOLS

(71) Applicant: ALDEXA THERAPEUTICS, INC., Burlington, MA (US)

(72) Inventors: Thomas A. Jordan, Lexington, MA (US); John Clifford Chabala, Scotch Plains, NJ (US); Ke-Qing Ling, Painseville, OH (US); William A. Kinney, Newtown, PA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 0 days.

(21) Appl. No.: 14/653,771

(22) PCT Filed: Dec. 19, 2013

(86) PCT No.: PCT/US2013/076592
§ 371 (c)(1),
(2) Date: Jun. 18, 2015

(87) PCT Pub. No.: WO2014/100425
PCT Pub. Date: Jun. 26, 2014

(65) Prior Publication Data
US 2015/0344432 A1    Dec. 3, 2015

Related U.S. Application Data

(60) Provisional application No. 61/740,197, filed on Dec. 20, 2012.

(51) Int. Cl.
*C07D 215/38* (2006.01)
*C07D 498/04* (2006.01)
*C07D 405/04* (2006.01)
*C07D 217/22* (2006.01)

(52) U.S. Cl.
CPC ......... *C07D 498/04* (2013.01); *C07D 215/38* (2013.01); *C07D 217/22* (2013.01); *C07D 405/04* (2013.01)

(58) Field of Classification Search
CPC .. C07D 215/38; C07D 217/22; C07D 405/04; C07D 498/04
See application file for complete search history.

(56) References Cited

U.S. PATENT DOCUMENTS

| | | | |
|---|---|---|---|
| 2,086,186 A | 7/1937 | Messer | |
| 5,472,954 A | 12/1995 | Loftsson | |
| 5,493,027 A | 2/1996 | Nichols et al. | |
| 5,668,117 A | 9/1997 | Shapiro | |
| 6,191,127 B1 | 2/2001 | Holscher | |
| 6,444,221 B1 | 9/2002 | Shapiro | |
| 6,498,154 B1 | 12/2002 | Grubb | |
| 7,973,025 B2 | 7/2011 | Jordan | |
| 7,982,071 B2 | 7/2011 | Scott | |
| 8,722,669 B2 | 5/2014 | Palczewski et al. | |
| 8,940,721 B2 | 1/2015 | Jordan | |
| 8,940,764 B2 | 1/2015 | Jordan | |
| 2004/0132636 A1 | 7/2004 | Dooley | |
| 2005/0020603 A1 | 1/2005 | Dai | |
| 2005/0090553 A1 | 4/2005 | Shapiro | |
| 2005/0130906 A1 | 6/2005 | Matier | |
| 2005/0197292 A1 | 9/2005 | Smithson | |
| 2005/0234018 A1 | 10/2005 | Lyons | |
| 2006/0014786 A1 | 1/2006 | Raut | |
| 2006/0111318 A1 | 5/2006 | Okamoto | |
| 2006/0183909 A1 | 8/2006 | Schmitt et al. | |
| 2006/0189608 A1 | 8/2006 | Bingaman | |
| 2007/0129404 A1 | 6/2007 | Hagihara | |
| 2007/0135481 A1 | 6/2007 | Jordan | |
| 2012/0108585 A1 | 5/2012 | Vu | |
| 2012/0302601 A1 | 11/2012 | Jordan | |
| 2014/0235604 A1 | 8/2014 | Palczewski et al. | |
| 2015/0209333 A1 | 7/2015 | Jordan | |
| 2015/0209345 A1 | 7/2015 | Jordan | |
| 2015/0335632 A1 | 11/2015 | Brady | |
| 2015/0344447 A1 | 12/2015 | Chabala | |

FOREIGN PATENT DOCUMENTS

| | | |
|---|---|---|
| EP | 0186367 A2 | 7/1986 |
| EP | 0245054 A1 | 11/1987 |
| EP | 0483881 A1 | 5/1992 |
| EP | 1621199 A1 | 1/2006 |
| EP | 2301549 A1 | 3/2011 |

(Continued)

OTHER PUBLICATIONS

Acland et al., "Gene Therapy Restores Vision in Canine Model of Childhood Blindness," Nature Genetics, 28:92-95 (2001).
Bernstein et al., "Retinal Toxicity Associated with Occupational Exposure to the Fish Anesthetic MS-222," American Journal of Ophthalmology, 124(6):843-844 (1997).
Bernstein et al., "Mechanism of Action of Aromatic Amines that Short Circuit the Visual Cycle," Biochemistry, 25:3370-3377 (1986).
Bernstein et al., "Short Circuiting the Visual Cycle with Retinotoxic Aromatic Amines," Proc Natl Acad Sci USA, 83:1632-1635 (1986).
Bernstein et al., "The Specific Inhibition of 11 cis-Retinyl Palmitate Formation in the Frog Eye by Diaminophenopentane, an Inhibitor of Rhodopsin Regeneration," Vision Research, 25(6):741-748 (1985).
Bucciantini et al., "Inherent Toxicity of Aggregates Implies a Common Mechanism for Protein Misfolding Diseases," Nature, 416:507-511 (2002).
Chapple et al., "Unfolding Retinal Dystrophies: A Role for Molecular Chaperones," Trends in Molecular Medicine, 7(9):414-421 (2001).

(Continued)

*Primary Examiner* — D M Seaman
(74) *Attorney, Agent, or Firm* — Andrea L. C. Reid; Dechert LLP

(57) ABSTRACT

The present invention is directed to compounds of formula (I):

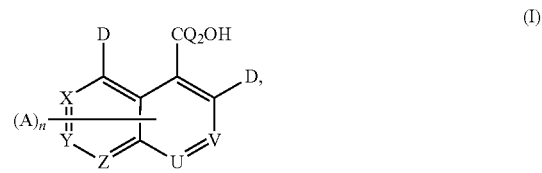

pharmaceutical compositions, and methods of use for treating, reducing a symptom of or reducing the risk of macular degeneration.

29 Claims, 2 Drawing Sheets

(56) References Cited

FOREIGN PATENT DOCUMENTS

| EP | 1888548 B1 | 8/2012 |
|---|---|---|
| JP | 2007532648 A | 11/2007 |
| JP | 2008542291 A | 11/2008 |
| SU | 509046 A1 | 6/1984 |
| WO | WO96/22992 A1 | 8/1996 |
| WO | WO-9805645 | 2/1998 |
| WO | WO99/46237 A1 | 9/1999 |
| WO | WO01/41757 A1 | 6/2001 |
| WO | WO2004/082622 A2 | 9/2004 |
| WO | WO2004/091630 A1 | 10/2004 |
| WO | WO2005/035506 A1 | 4/2005 |
| WO | WO2005/079774 A2 | 9/2005 |
| WO | WO2005/105067 A2 | 11/2005 |
| WO | WO-2006002473 A1 | 1/2006 |
| WO | WO2006/049968 A1 | 5/2006 |
| WO | WO2006/127945 A1 | 11/2006 |
| WO | WO2007/118276 A1 | 10/2007 |
| WO | WO2008/014602 A1 | 2/2008 |
| WO | WO2010/133672 A1 | 11/2010 |
| WO | WO-2011008202 A1 | 1/2011 |
| WO | WO-2011071995 A2 | 6/2011 |
| WO | WO-2012097173 A2 | 7/2012 |
| WO | WO-2012105887 A1 | 8/2012 |
| WO | WO2014/116593 A1 | 7/2014 |
| WO | WO2014116836 A2 | 7/2014 |
| WO | WO-2015187942 A1 | 12/2015 |
| WO | WO-2016085939 A2 | 6/2016 |

OTHER PUBLICATIONS

Conover et al., Thiazole analogs of pyridoxine, Journal of the American Chemical Society, 72(110:5221-5225 (1950).

De Jong, Paulus, "Age-Related Macular Degeneration," The New England Journal of Medicine, 355:1474-1485 (2006).

Dowling J.E., "Neural and Photochemical Mechanisms of Visual Adaptation in the Rat," Journal of General Physiology, 46:1287-1301 (2006).

Drysdale et al., "Complex Promoter and Coding Region β2-Adrenergic Receptor Haplotypes Alter Receptor Expression and Predict in vivo Responsiveness," Proceedings of the National Academy of Sciences USA, 97(19):10483-10488 (2000).

Fowler et al., "Colored Complexes of all-trans-retinal with Bezocaine and Other Local Anesthetics," Journal of Photochemistry and Photobiology B: Biology, 8:183-188 (1991).

Hubbard, R., "Geometrical Isomerization of Vitamin A, Retinene and Retinine Oxime," Journal of the American Chemical Society, 78:4662-4667 (1956).

Hurd et al., "Reaction of propiolactone with aniline derivatives," Journal of the American Chemical Society, 74:5889-5891 (1952).

Ito, N. et al., "A medium-term rat liver bioassay for rapid in vivo detection of carcinogenic potential of chemicals," Cancer Science, 94(1):3-8 (2003).

Karan et al., "Lipofuscin accumulation, abnormal electrophysiology, and photoreceptor degeneration in mutant ELOVL4 transgenic mic: a model for macular degeneration," Proceedings of the National Academy of Sciences USA, 102(11):4164-4169 (2005).

Landor, S. et al., "Allenes. Part 49. 1 4-Amino-2-(1 hydroxyalkyl) quinolines from PHenylhdroxylamine and Allenic Nitriles," J Chem Soc., Perkin Trans, 251-254 (1989).

Li et al., "Effect of Vitamin A supplementation on rhodopsin mutants threonine-17→methionine and proline-347→Serine in transgenic mice and in cell cultures," Proc. Natl. Acad. Sci. USA 95:11933-11938 (1998).

Nema et al., "Excipients and Their Use in Injectable Products," PDA Journal of Pharmaceutical Science and Technology, 51(4): 166-171 (1997).

Nerurkar et al., "β-arylglutaconic acids. II. Imides of certain P-arylglutaconic and glutaric acids," Journal of Organic Chemistry, 24:2055-2056 (1959).

Noorwez et al., "Pharmacological chaperone-mediated in vivo folding and stabilization of the P23H-opsin mutant associated with autosomal dominant retinitis pigmentosa," Journal of Biological Chemistry, 278(16):14442-14450 (2003).

Organisciak et al., "Susceptability to retinal light damage in transgenic rats with rhodopsin mutations," Investigative Ophthalmology & Visual Science, 44:486-492 (2003).

Parish et al., "Isolation and one-step preparation of A2E and iso-A2E, fluorophores from human retinal pigment epithelium," Proceedings of the National Academy of Sciences USA, 95:14609-14613 (1998).

Radu et al., "Treatment with isoretinin inhibits lipofuscin accumulation in a mouse model of recessive Stargardt's macular degeneration," Proc Natl Acad Sci. USA, 100(8):4742-4747 (2003).

Rapp et al., "The effects of local anesthetics on retinal function," Vision Research, 22:1097-1103 (1982).

Sherman et al., "Cellular defenses against unfolded proteins: a cell biologist thinks about neurodegenerative diseases," Neuron, 29:15-32 (2001).

Sieving et al., "Inhibition of the visual cycle in vivo by 12-cis retinoic acid protects from light damage and provides a mechanism for night blindness in isoretinin therapy," Proceedings of the National Academy of Sciences USA, 98(4):1835-1840 (2001).

Snell et al., "Novel structure having antagonist actions at both the glycine site of the N-Methyl-DAspartate receptor and neuronal voltage-sensitive sodium channels: biochemical, electrophysiological, and behavioral characterization," Journal of Pharmacology and Experimental Therapeutics, 292(0:215-227 (2000).

Ueda et al., "Evaluation of sulfobutyl ether beta-cyclodextrin as a stabilizing/solubilizing agent for several drugs," Drug Dev. Ind. Pharm. 24:863-7 (1998).

Vlaskina et al., "Novel synthesis of substituted benzimidazoles by reduction of esters of 4-alkylamino-3, 5-dinitro-benzoic acids by tin chloride," Chemistry of Heterocyclic Compounds, 40(4):523-524 (2004).

Wang et al., "A facile one-pot synthesis of 2-substituted-3-aminoquinolines: preparation of benzo[b]naphthyridine-3-carbonitriles," Tetrahedron, 60(13):2937-2942 (2004).

Weng et al., "Insights into the function of Rim protein in photoreceptors and etiology of Stargardt's disease from the phenotype in abcr knockout mice," Cell, 98:13-23 (1999).

Westphal et al., "Reactions with pyridinium pyruvic acid esters," Pharmazie, 31(11): 770-773 (1976).

English Translation of: Westphal et al., Pharmazie, 31(11): 770-773 (1976).

Wolkenberg et al., Design, Synthesis, and Evaluation of Novel 3,6 Diaryl-4-aminoalkoxyquinolones as Selective Agonists of Somatostatin Receptor Subtype 2, J Med. Chem. 54:2351-2358 (2011).

U.S. Appl. No. 14/760,039.

U.S. Appl. No. 14/760,041.

Sparrow et al., "Phospholipid meets all-trans-retinal: the making of RPE bisretinoids," J. Lipid Res.51(2):247-61 Epub Aug. 7, 2009.

International Search Report for International Application No. PCT/US2013/076592, dated Apr. 30, 2014.

International Preliminary Report on Patentability for International Application No. PCT/US2013/076592, dated Jul. 18, 2014.

Radu et al., "Isotretinoin treatment inhibits lipofuscin accumulation in a mouse model of recessive Stargardt's macular degeneration," Novartis Foundation Symposium 25:51-63 (2004) (Abstract Only).

Yarnell, A., "Light flips the lipid switch," C&EN, 82(29):22-23 (2004).

Atkinson et al., 1966, "Triazaphenanthrenes. Part VI.* Further Observations on the Widman-Stoermer and Brosche Reactions," Journal of Chemical Society, pp. 2053-2060.

Godard et al., 1980, "Sur les orthoamino formyl quinoléines, nouveaux synthons hétérocycliques," Journal of Heterocyclic Chemistry, 17(3):465-473.

Grob et al., 1950, "Die Synthese von 5-Oxy-benz(cd)indolin und dessen Umpagerung in 5-Keto-1,3,4,5-tetrahydro-benz(cd)indol," Helvetica Chimica Acta, Verlag Helvetica Chimica Acta, Ch, 33(6):1796-1808.

Supplementary European Search Report issued by the European Patent Office for European Patent Application No. EP13865015.5 mailed Mar. 31, 2016 (9 pages).

(56) References Cited

OTHER PUBLICATIONS

Tian et al., 2012, "First total synthesis and determination of the absolute configuration of 1-N-methyl-3-methylamino-[N-butanoicacid-3-(9-methyl-8-propen-7-one)-amide]-benzo[f][1,7]naphthyridine-2-one, a novel benzonaphthyridine alkaloid," Tetrahedron Letters, 53:4892-4895.

Search Report and Written Opinion issued by the Intellectual Property Office of Singapore for Singapore Application No. 11201504859Y mailed Aug. 1, 2016 (12 pages).

Aldini et al., "Lipoxidation-Derived Reactive Carbonyl Species as Potential Drug Targets in Preventing Protein Carbonylation and Related Cellular Dysfunction," ChemMedChem, vol. 1, No. 10, Dec. 2006 (pp. 1045-1058).

Burcham et al., "Aldehyde-Sequestering Drugs: Tools for Studying Protein Damage by Lipid Peroxidation Products," Toxicology, vols. 181-182, Dec. 27, 2002 (pp. 229-236).

Negre-Salvayre et al., "Advanced Lipid Peroxidation End Products in Oxidative Damage to Proteins. Potential Role in Diseases and Therapeutic Prospects for the Inhibitors," British Journal of Pharmacology, vol. 153, No. 1, Jan. 2008 (pp. 6-20).

Supplementary Partial European Search Report issued by the European Patent Office for European Patent Application No. 14743711.5 mailed Jul. 20, 2016 (14 pages).

Search Report and Written Opinion issued by the Intellectual Property Office of Singapore for Singapore Patent Application No. 11201505587Y mailed Jul. 12, 2016 (12 pages).

Voziyan et al., "A Post-Amadori Inhibitor Pyridoxamine also Inhibits Chemical Modification of Proteins by Scavenging Carbonyl Intermediates for Carbohydrate and Lipid Degradation," The Journal of Biological Chemistry, vol. 277, No. 5, Feb. 1, 2002 (pp. 3397-3403).

Wood et al., "Aldehyde Load in Ischemia-Reperfusion Brain Injury: Neuroprotection by Neutralization of reactive Aldehydes with Phenelzine," Brain Research, vol. 1122, No. 1, Nov. 29, 2006 (pp. 184-190).

Zagol-Ikapitte et al., "Characterization of scavengers of γ-ketoaldehydes that do not inhibit prostaglandin biosynthesis," Chemical Research in Toxicology, vol. 23, No. 1, Jan. 2010 (pp. 240-250).

Godard et al., 1980, "Sur les orthoamino formyl quinoléines, nouveaux synthons hétérocycliques," Journal of Heterocyclic Chemistry, 17(3):465-473.

Thian et al., 2012, "First total synthesis and determination of the absolute configuration of 1-N-methyl-3-methylamino-[N-butanoicacid-3-(9-methyl-8-propen-7-one)-amide]-benzo[f][1,7]naphthyridine-2-one, a novel benzonaphthyridine alkaloid," Tetrahedron Letters, 53:4892-4895.

PERI-CARBINOLS

CROSS-REFERENCE TO RELATED APPLICATION

This application is a National Stage of International Application No. PCT/US2013/076592, filed on Dec. 19, 2013, which claims the benefit under 35 U.S.C. 119(e) of U.S. Provisional Application No. 61/740,197, filed on Dec. 20, 2012, the contents of which are incorporated herein in their entirety.

BACKGROUND OF THE INVENTION

Macular degeneration is a leading cause of progressive blindness. The macula is the central region of the retina and contains the fovea where high acuity central vision is processed. Macular degeneration is a neurodegenerative disease in the macula that progressively causes disabling deficits in central vision which is processed by foveal cone photoreceptors, in night vision which is processed by rod photoreceptors, and in dark adaptation under conditions of both daylight (cones) and darkness (rods).

There are multiple forms of macular degeneration. Dry age-related macular degeneration (AMD) is the initial and most common form and first appears at middle age or later. Its clinical signs include an increase in fundus auto-fluorescence (FAF) and the formation of extracellular deposits called soft drusen, both caused by the accumulation of lipofuscin in retinal pigment epithelial (RPE) cells as discussed below. About 40% of dry AMD patients progress to an advanced form of the disease called geographic atrophy (GA), secondary to dry AMD, characterized by one or more atrophic retinal lesions caused by the localized death of RPE cells and adjacent retinal photoreceptor cells. Another 10% of dry AMD patients progress to wet AMD, characterized by neovascular growth from the choroid into the retina, which disrupts retinal tissue and thereby destroys visual function. Finally, there is an early onset form of macular degeneration called Stargardt's disease, which first appears in teenagers and young adults. Stargardt's disease is believed to have the same etiology as dry AMD, but does not involve choroidal neovascularization as it progresses.

Multiple lines of evidence indicate that macular degeneration is caused by the gradual accumulation in RPE cells of a naturally occurring bis-retinoid compound called A2E (J. R. Sparrow et al., Phospholipid meets all-trans-retinal: the making of RPE bisretinoids, J. Lipid Res., Aug. 7, 2009). A2E is a cytotoxic product from the reaction of all-trans retinaldehyde (RAL) and phosphatidylethanolamine (PE), a membrane phospholipid found in the disc membranes of photoreceptor outer segments. The RAL that reacts with PE escapes from the visual cycle (step 3b in FIG. 1), a metabolic pathway in the back of the eye. The visual cycle (i) converts vitamin A from an alcohol (retinol) to a photo-reactive aldehyde (11-cis-retinaldehyde) for use in photo-transduction by opsin proteins in photoreceptor cell outer segments, and (ii) converts RAL to retinol after photo-transduction. As RAL escapes the visual cycle, A2E precursors form reversibly in photoreceptor outer segments, which are ingested by neighboring RPE cells after diurnal shedding. The final and irreversible step in the biosynthesis of A2E takes place in the acidic environment of RPE cell lysosomes.

As A2E accumulates in RPE cells, it gradually poisons them by multiple mechanisms including lysosomal failure and oxidative stress. Lysosomal failure leads to the accumulation of undigested cellular debris called lipofuscin, which contains A2E and can be detected clinically by FAF imaging. Oxidative stress leads to RPE cell death by apoptotic mechanisms in GA, and triggers VEGF signaling by RPE cells which causes the choroidal neovascular growth that is the hallmark of wet AMD. Complement cascades are activated by oxidized A2E in drusen and cause further pathology by inflammatory pathways. As RPE cells deteriorate, they lose their ability to participate in the visual cycle and are unable to provide photoreceptors with the metabolic support required for normal visual function. As this metabolic support is withdrawn, photoreceptors fail to renew their shed outer segments and visual function is progressively lost. By reducing the formation of A2E pharmacologically, RPE cells can recover from A2E toxicities and resume their normal metabolic support of photoreceptor cells.

The PCT publication WO 2006/127945 discloses compounds and compositions that have been shown to reduce the formation of A2E. Those compounds are designed to inhibit A2E biosynthesis by reducing the amount of free RAL available for reaction with PE in photoreceptor outer segments. However, there still exists a need for more potent compounds. The present application addresses that need.

SUMMARY OF THE INVENTION

The invention relates to compounds, pharmaceutical compositions and methods for treating, reducing a symptom of or reducing the risk of developing a retinal disease or disorder in which accumulation of A2E and/or lipofuscin in retinal tissue or VEGF signaling by RPE cells in response to oxidative stress is involved.

The invention relates to a compound of formula (I):

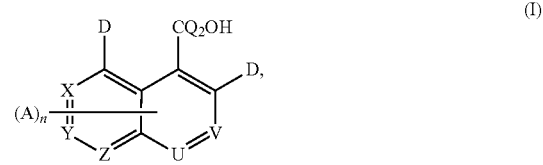

or a pharmaceutically acceptable salt thereof, wherein:

each D is independently H, $NH_2$ or A, provided that one D is $NH_2$ and the other D is H or A;

U, V, Z, Y and X are each independently CH, CA or N, provided that only one of U, V, Z, Y and X is N;

each A is independently selected from F, Cl, Br, $CF_2H$, $CF_3$, R', OR, COOR, $CON(R)_2$, $N(R')_2$, NRCOR, NRCOOR', $NRCON(R)_2$, $NRSO_2R'$, $SO_2R'$, $SO_2N(R)_2$, unsubstituted phenyl, and phenyl substituted with 1-3 substituents, wherein each substituent is independently selected from F, Cl, $CF_2H$, $CF_3$, OR and R', or two such substituents, together with the carbon atoms of the phenyl ring to which they are attached, form a five- or six-membered ring having a structure selected from

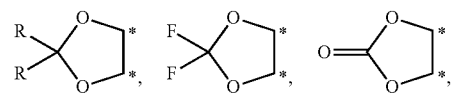

-continued

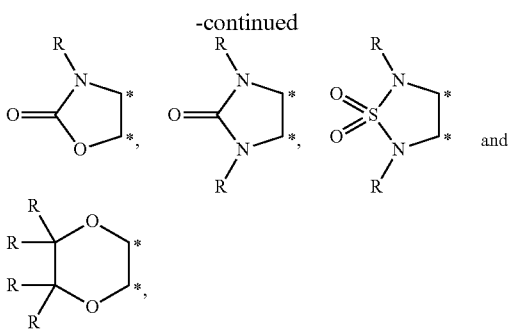

wherein "*" denotes the positions of the carbon atoms to which the substituents are attached on the phenyl ring, alternatively, when attached to adjacent atoms in formula (I), any two A, together with the atoms to which they are attached, form a five- or six-membered ring having a structure selected from

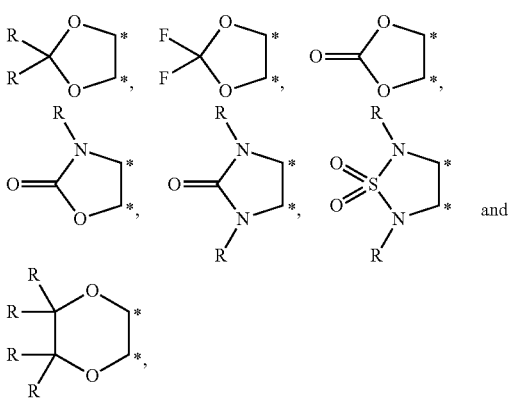

wherein "*" denotes the positions of the atoms to which the two A are attached on formula (I);

each R is independently H, straight chain $C_{1-6}$-alkyl, branched $C_{3-6}$-alkyl or cyclic $C_{3-6}$-alkyl;

each R' is independently straight chain $C_{1-6}$-alkyl, branched $C_{3-6}$-alkyl or cyclic $C_{3-6}$-alkyl;

each $R_Q$ is independently H, straight chain $C_{1-6}$-alkyl, branched $C_{3-6}$-alkyl or halogen;

each Q is independently H, straight chain $C_{1-6}$-alkyl or branched $C_{1-6}$-alkyl, wherein the alkyl is optionally substituted with 1-6 F, or both Q, together with the carbon atom to which they are attached, form a $C_{3-6}$-carbocycle or a saturated heterocycle selected from

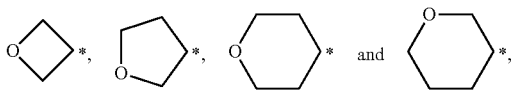

wherein "*" denotes the position of the carbon atom to which both Q are attached, wherein the carbocycle or the heterocycle is optionally substituted with one or more $R_Q$; and n is 0, 1, 2, or 3.

The invention also relates to a pharmaceutical composition comprising a compound of formula (I) or a pharmaceutically acceptable salt thereof, and a pharmaceutically acceptable excipient or carrier.

The invention also relates to a method of treating, reducing a symptom of or reducing the risk of developing a retinal disease or disorder in which accumulation of A2E and/or lipofuscin in retinal tissue or VEGF signaling by RPE cells in response to oxidative stress is involved.

Unless otherwise defined, all technical and scientific terms used herein have the same meaning as commonly understood by one of ordinary skill in the art to which this invention belongs. In the case of conflict, the present specification, including definitions, will control. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the invention. In addition, the materials, methods, and examples are illustrative only and are not intended to be limiting.

Other features and advantages of the invention will be apparent from the following detailed description and claims.

DETAILED DESCRIPTION OF THE INVENTION

The invention provides heteroaryl compounds of formula (I), which have a carbinol moiety, $CQ_2OH$, and are unsubstituted or substituted with a substituent, A, at a position which is in a peri-relationship as shown below. These compounds can be effective (e.g., even more effective than the compounds previously described, such as those described in WO 2006/127945) in trapping RAL and reducing A2E formation.

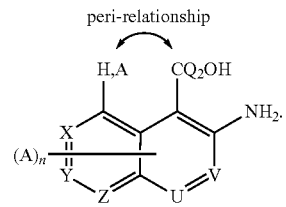

Figure 1:
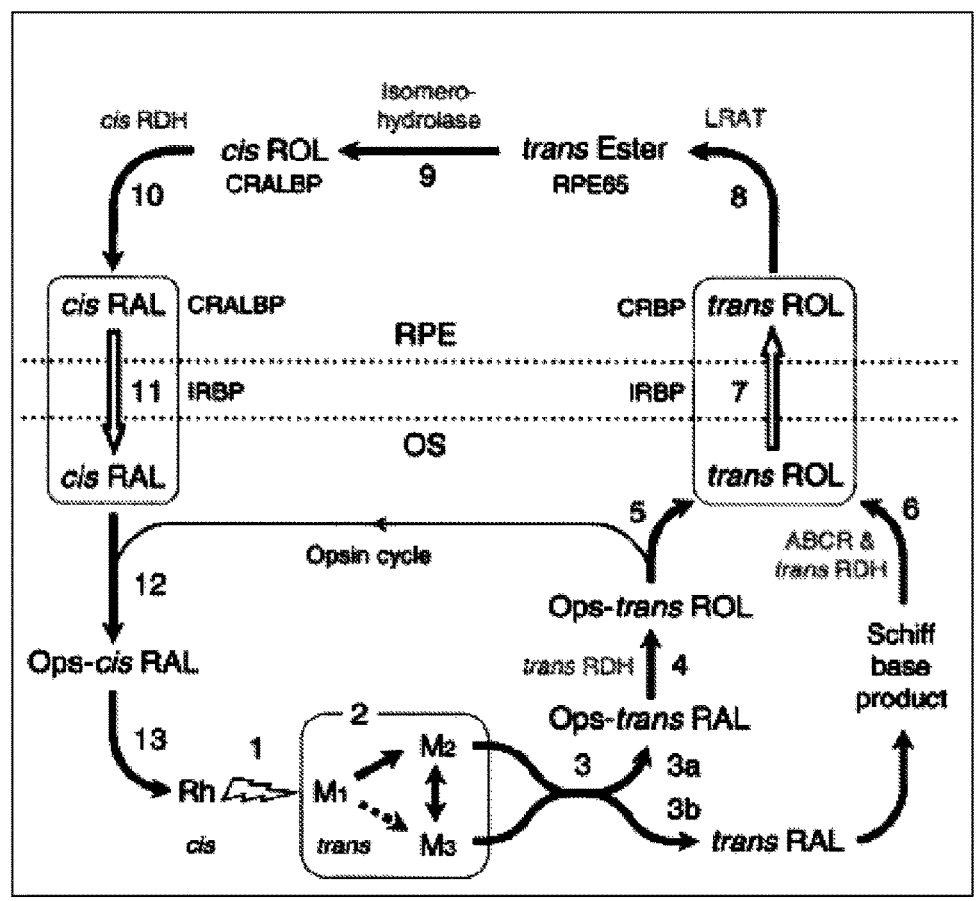
FIG. 1 is a scheme showing the visual cycle.
Figure 2:
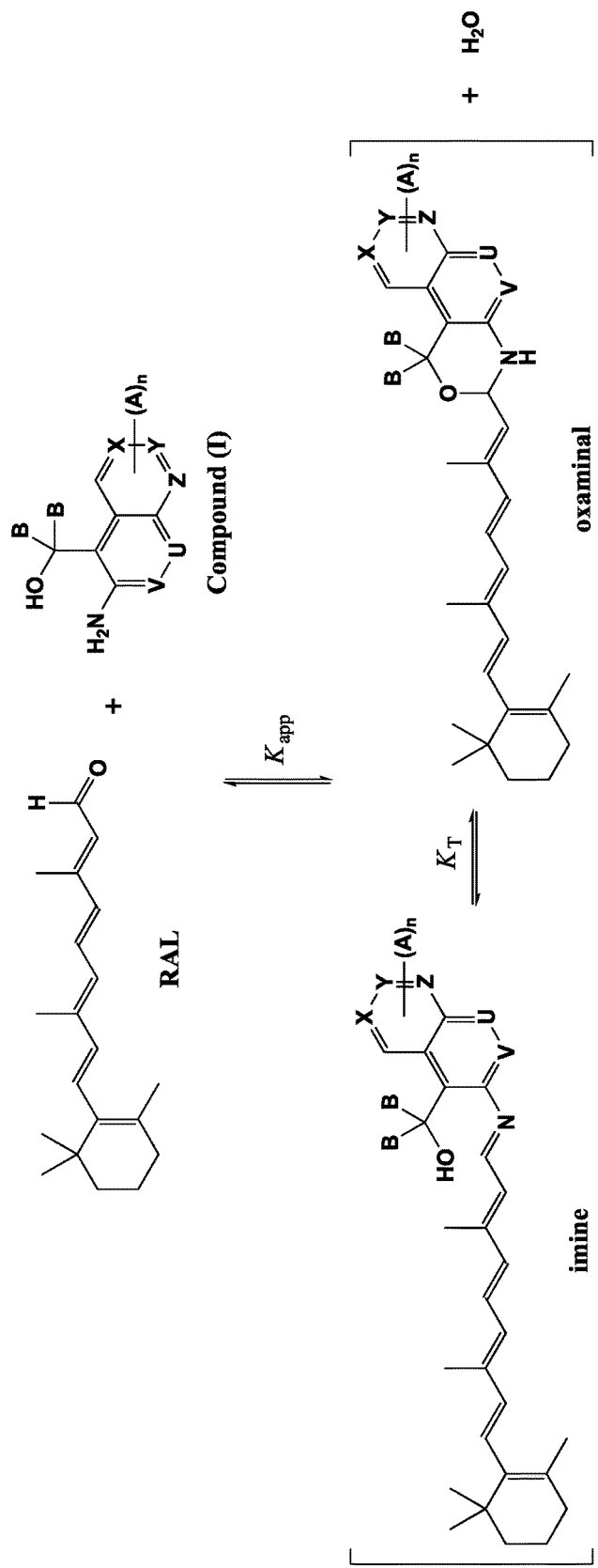
FIG. 2 is a scheme showing the reaction of RAL with a compound of the invention.

In reaction with exogenous RAL in an in vitro preparation of isolated rod photoreceptor outer segments, representative compounds of this invention have more favorable reaction energetics and equilibrium constants ($K_{app}$) which are shifted toward imine and oxaminal product formation to a large extent; and the equilibrium ($K_T$) is shifted far to the oxaminal product, thus making the compounds of the invention more effective RAL traps. (FIG. 2 and Table 1)

The invention relates to compounds, pharmaceutical compositions and methods for treating, reducing a symptom of or reducing the risk of developing a retinal disease or disorder in which accumulation of A2E and/or lipofuscin in retinal tissue or VEGF signaling by RPE cells in response to oxidative stress is involved. For example, the invention relates to compounds, pharmaceutical compositions and methods for treating, reducing a symptom of or reducing the risk of developing macular degeneration and other retinal diseases or disorders caused by accumulation of A2E and/or lipofuscin in retinal tissue or by VEGF signaling by RPE cells in response to oxidative stress.

Specifically the invention is directed to the compounds of formula (I), pharmaceutical compositions and methods of use thereof.

The invention is directed to a compound of formula (I):

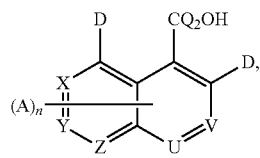

(I)

or a pharmaceutically acceptable salt thereof, wherein:

each D is independently H, $NH_2$ or A, provided that one D is $NH_2$ and the other D is H or A;

U, V, Z, Y and X are each independently CH, CA or N, provided that only one of U, V, Z, Y and X is N;

each A is independently selected from F, Cl, Br, $CF_2H$, $CF_3$, R', OR, COOR, $CON(R)_2$, $N(R')_2$, NRCOR, NRCOOR', $NRCON(R)_2$, $NRSO_2R'$, $SO_2R'$, $SO_2N(R)_2$, unsubstituted phenyl, and phenyl substituted with 1-3 substituents, wherein each substituent is independently selected from F, Cl, $CF_2H$, $CF_3$, OR and R', or two such substituents, together with the carbon atoms of the phenyl rings to which they are attached, form a five- or six-membered ring having a structure selected from

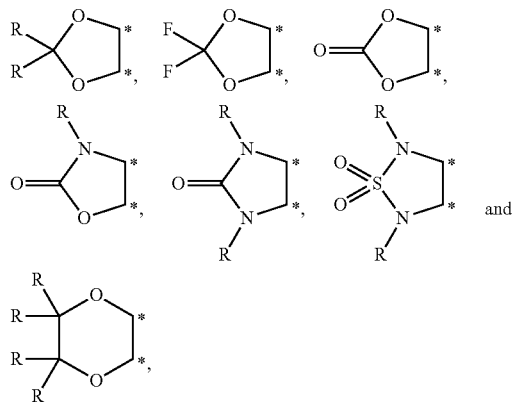

wherein "*" denotes the positions of the carbon atoms to which the substituents are attached on the phenyl ring, alternatively, when attached to adjacent atoms in formula (I), any two A, together with the atoms to which they are attached, form a five- or six-membered ring having a structure selected from

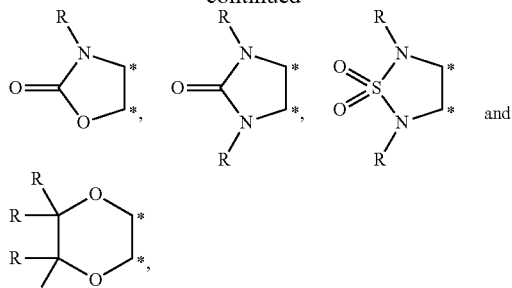

wherein "*" denotes the positions of the atoms to which the two A are attached on formula (I);

each R is independently H, straight chain $C_{1-6}$-alkyl, branched $C_{3-6}$-alkyl or cyclic $C_{3-6}$-alkyl;

each R' is independently straight chain $C_{1-6}$-alkyl, branched $C_{3-6}$-alkyl or cyclic $C_{3-6}$-alkyl;

each $R_Q$ is independently H, straight chain $C_{1-6}$-alkyl, branched $C_{3-6}$-alkyl or halogen;

each Q is independently H, straight chain $C_{1-6}$-alkyl or branched $C_{3-6}$-alkyl, wherein alkyl is optionally substituted with 1-6 F, or both Q, together with the carbon atom to which they are attached, form a $C_{3-6}$-carbocycle or a saturated heterocycle selected from

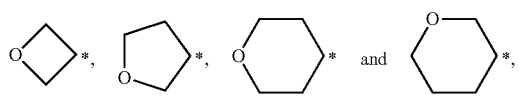

wherein "*" denotes the position of the carbon atom to which both Q are attached, wherein the carbocycle or the heterocycle is optionally substituted with one or more $R_Q$; and n is 0, 1, 2, or 3.

In one embodiment of the invention, the compounds are quinoline or isoquinoline compounds, exemplified by the compounds of one of formulae (II)-(VII):

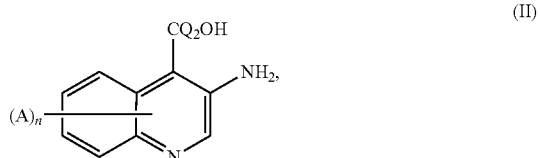

(II)

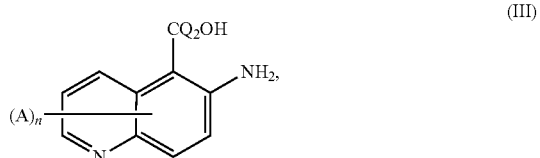

(III)

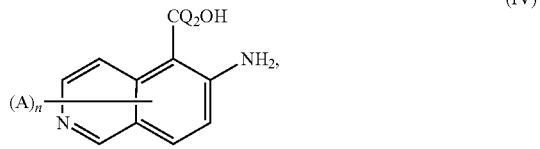

(IV)

-continued

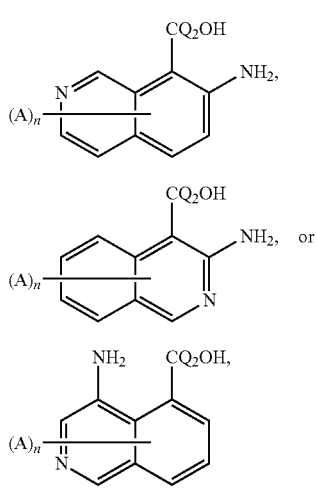

or a pharmaceutically acceptable salt thereof.

Further exemplifying this embodiment are the compounds of one of formulae (II), (III), (IV), (V) and (VII):

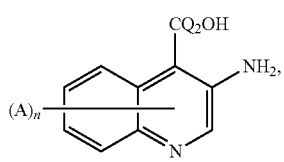
(II)

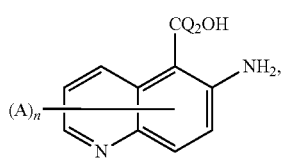
(III)

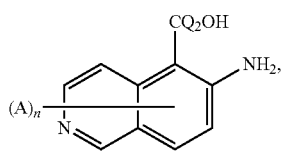
(IV)

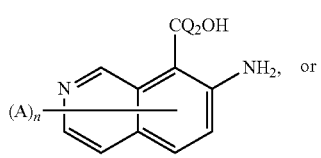
(V)

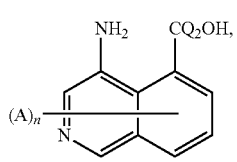
(VII)

or a pharmaceutically acceptable salt thereof.

Specifically exemplifying this embodiment are the compounds of formula (II):

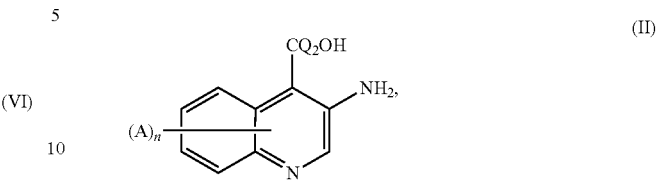
(II)

or a pharmaceutically acceptable salt thereof.

Further illustrating this exemplification are the compounds of formula (II), wherein n is 0, 1 or 2. Yet a further illustration includes the compounds of formula (II) wherein A, which can be attached to either ring of formula (II), is F or Cl. Further defining formula (II) are the compounds wherein Q is selected from straight chain $C_{1-6}$ alkyl or branched $C_{3-6}$ alkyl, or wherein both Q, together with the carbon atom to which they are attached, form a ring selected from

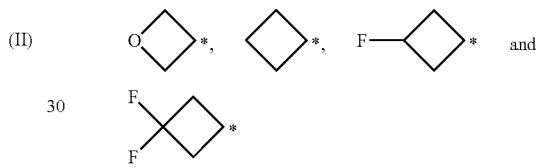

wherein "*" denotes the position of the carbon atom to which both Q are attached.

Specific examples of formula (II) include compounds (a)-(h) and pharmaceutically acceptable salts thereof:

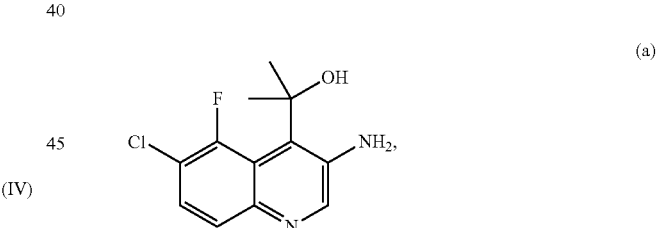
(a)

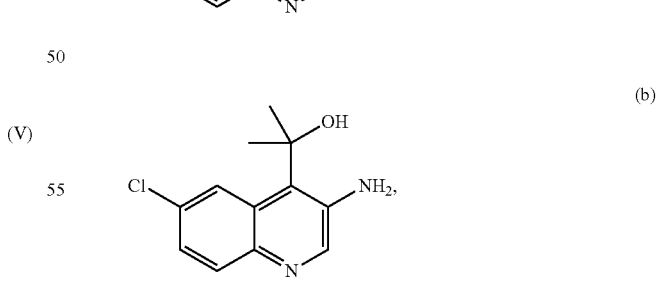
(b)

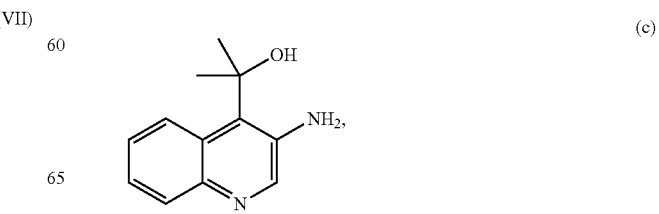
(c)

-continued

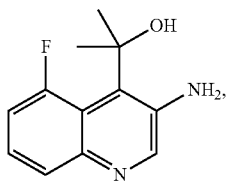
(d)

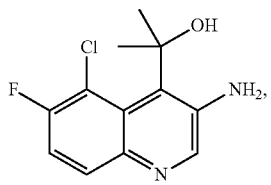
(e)

(f)

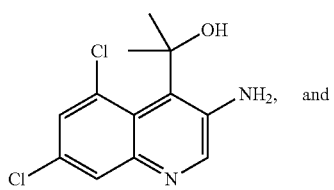
(g)

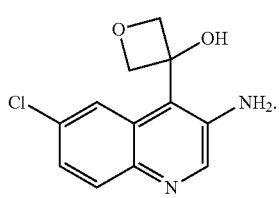
and

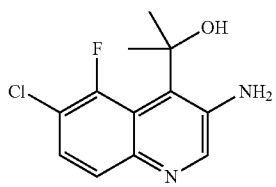
(h)

Compounds (a) and (b) even further define this group:

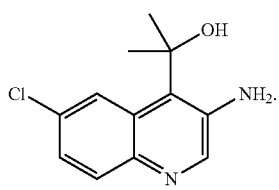
(a)

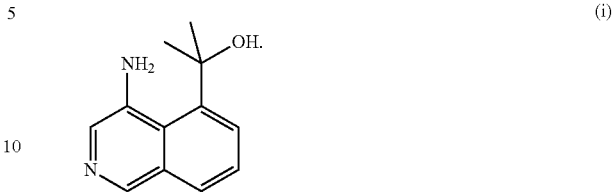
(b)

Yet further illustrating this exemplification are the compounds of formula (VII) wherein n is 0 and each Q is methyl.

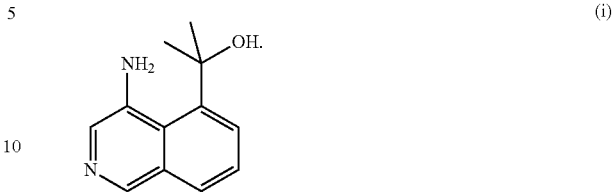
(i)

Examples of the compounds of the invention include a compound of formula (I), wherein U is N, or V is N, or Z is N, or X is N, or Y is N. For example, U is N. For example, Y is N.

Examples of the compounds of the invention include a compound of formula (I), wherein one D is $NH_2$ and the other D is H or F, or Cl. For example, one D is $NH_2$ and the other D is H. For example, one D is $NH_2$ and the other D is F or Cl.

Examples of the compounds of the invention include a compound of any one of formulae (I)-(VII), wherein n is 0, 1 or 2. For example, n is 1.

Examples of the compounds of the invention include a compound of any one of formulae (I)-(VII), wherein each A is independently selected from F, Cl, Br, $CF_2H$, $CF_3$, R', OR, COOR, $CON(R)_2$, $N(R')_2$, NRCOR, NRCOOR', $NRCON(R)_2$, $NRSO_2R'$, $SO_2R'$, $SO_2N(R)_2$, unsubstituted phenyl, and phenyl substituted with 1-3 substituents as listed above. For example, each A is independently selected from F, Cl, Br, $CF_2H$, $CF_3$ and R'. For example, each A is independently selected from F, Cl and Br. For example, n is 0, 1 or 2 and each A is independently selected from F, Cl, Br, $CF_2H$, $CF_3$, R', OR, COOR, $CON(R)_2$, $N(R')_2$, NRCOR, NRCOOR', $NRCON(R)_2$, $NRSO_2R'$, $SO_2R'$, $SO_2N(R)_2$, unsubstituted phenyl, and phenyl substituted with 1-3 substituents as listed above. For example, n is 0, 1 or 2 and each A is independently selected from F, Cl, Br, $CF_2H$, $CF_3$ and R'. For example, n is 0, 1 or 2 and each A is independently selected from F, Cl and Br.

Examples of the compounds of the invention include a compound of any one of formulae (I)-(VII), wherein at least one Q is straight chain $C_{1-6}$-alkyl. For example, in certain compounds, at least one Q is methyl, ethyl or propyl. For example, each Q is methyl. For example, n is 0, 1 or 2 and at least one Q is straight chain $C_{1-6}$-alkyl (e.g., methyl, ethyl and propyl). For example, n is 0, 1 or 2 and each Q is methyl. In another example, at least one Q is straight chain $C_{1-6}$-alkyl substituted with 1-6 F. For example, in certain compounds, at least one Q is methyl, ethyl or propyl substituted with 1-6 F. For example, at least one Q is $CH_2F$, $CHF_2$, or $CF_3$. For example, each Q is $CF_3$. For example, n is 0, 1 or 2 and at least one Q is straight chain $C_{1-6}$-alkyl substituted with 1-6 F (e.g., methyl, ethyl or propyl substituted with 1-6 F). For example, n is 0, 1 or 2 and each Q is $CF_3$.

Examples of the compounds of the invention include a compound of any one of formula (I)-(VII), wherein both Q, together with the carbon atom to which they are attached, form a $C_{3-6}$ carbocycle or a saturated heterocycle, each of which is optionally substituted with one or more $R_Q$, wherein each $R_Q$ is independently methyl, ethyl, propyl, fluorine, chlorine or bromine (e.g., each $R_Q$ is independently methyl or fluorine). For example, both Q, together with the carbon atom to which they are attached, form

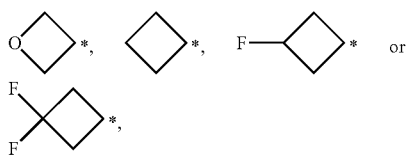

wherein "*" denotes the position of the carbon atom to which the two Q are attached.

Examples of the compounds of the invention include a compound of any one of formula (I)-(VII), wherein each R is independently H or straight chain $C_{1-6}$-alkyl. For example, each R is independently H, methyl, ethyl or propyl.

Examples of the compounds of the invention include a compound of any one of formula (I)-(VII), wherein each R' is independently methyl, ethyl or propyl.

In some exemplifications, the compounds of the invention react with RAL to form imine and oxaminal tautomers. Further illustrating this exemplification, the reaction of the compounds of the invention with RAL has a reaction equilibrium constant ($K_T$) which favors the formation of the oxaminal tautomer over the imine tautomer. For example, the equilibrium concentration of the oxaminal tautomer is higher than the equilibrium concentration of the imine tautomer, e.g., at least 2-fold higher, 5-fold higher, 10-fold higher, 50-fold higher, 100-fold higher, 500-fold higher, or 1000-fold higher. In some examples, the compounds of the invention react with RAL and form the oxaminal tautomer at an equilibrium concentration which is 500-1000 fold higher than the equilibrium concentration of the imine tautomer.

Representative compounds of the invention include compounds listed in the table below.

A second aspect of the invention is directed to a method of treating, reducing a symptom of or reducing the risk of a retinal disease or disorder in which accumulation of A2E and/or lipofuscin in retinal tissue or VEGF signaling by RPE cells in response to oxidative stress is involved. For example, the invention is directed to a method of treating, reducing a symptom of or reducing the risk of macular degeneration and other retinal diseases or disorders caused by accumulation of A2E and/or lipofuscin in retinal tissue or by VEGF signaling by RPE cells in response to oxidative stress, including dry age-related macular degeneration (AMD), geographic atrophy (GA) secondary to dry AMD, wet AMD and Stargardt's disease. The method includes administering a pharmaceutical composition comprising a compound of the invention, such as a compound of formula (I), to a subject in need thereof, such as a patient having or being at a risk of developing macular degeneration or a retinal disease or disorder in which accumulation of A2E and/or lipofuscin in retinal tissue or VEGF signaling by RPE cells in response to oxidative stress is involved. Exemplifying this aspect is a method of treating, reducing a symptom of or reducing the risk of macular degeneration, dry AMD or GA secondary to dry AMD. Also exemplifying this aspect is a method of treating, reducing a symptom of or reducing the risk of wet AMD. This aspect is also exemplified by a method of treating, reducing a symptom of or reducing the risk of Stargardt's disease.

In the methods of the invention, the level of A2E should be lowered relative to that in the subject (e.g., a patient) prior to the administration of a composition comprising a compound of the invention, such as a compound of formula (I). More specifically, the method comprises administering the composition wherein the compound of formula (I) is selected from:

(a)
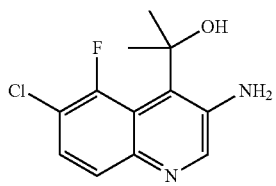

(b)
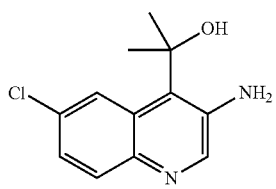 [SMILES: CC(C)(O)c1c(N)cnc2ccc(Cl)cc12]

(c)
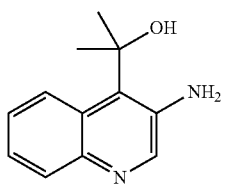

(d)
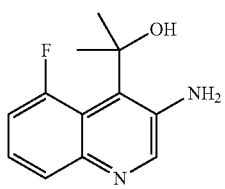 [SMILES: CC(C)(O)c1c(N)cnc2cccc(F)c12]

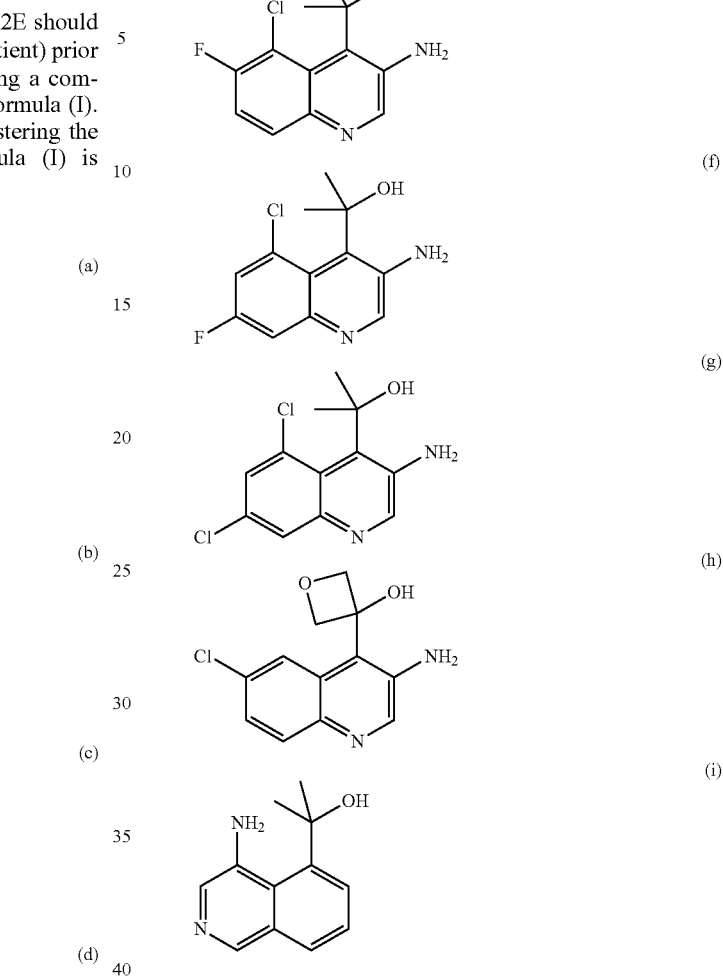

or a pharmaceutically acceptable salt thereof.

It should be understood that each form of macular degeneration may be treated in the method of the invention.

The compounds of the invention may be readily prepared by those skilled in the art. In particular the compounds of the invention may be prepared following the schemes illustrated below:

General Synthesis Scheme 2

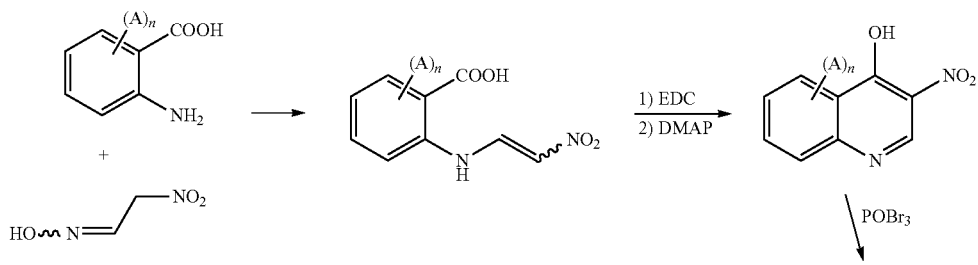

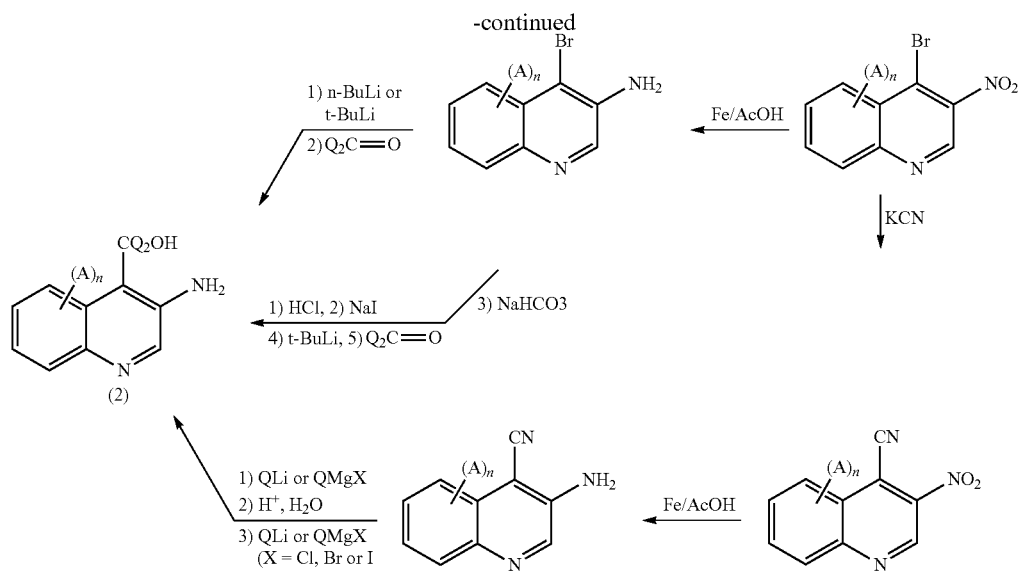

EDC: N-ethyl-N'-(3-dimethylamino)propylcarbodiimide;
DMAP: 4-dimethylaminopyridine Compounds of formula (II) can be synthesized according to Scheme 2.

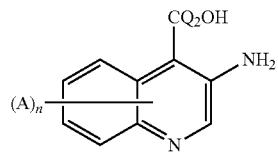

As shown in Scheme 2, compounds of formula (II) are prepared from 3-nitro-4-bromoquinolines (prepared by reaction of anthranilic acids with methazonic acid) by reduction of the nitro group to an amine group, followed by debromolithiation of the bromide with an alkyllithium reagent and reaction with ketones ($Q_2C=O$). In some instances, the 4-bromide is converted to a 4-iodide prior to dehalolithiation. In other instances, the bromine of the 3-nitro-4-bromoquinolines is displaced by cyanide anion and then the nitro group is reduced to provide 3-amino-4-cyanoquinolines. The 3-amino-4-cyanoquinolines are then treated with alkyllithium or alkyl Grignard reagents and hydrolyzed with aqueous acid to provide 1-(3-aminoquinolin-4-yl)alkan-1-ones, which are again treated with an alkyllithium or alkyl Grignard reagents to provide compounds of formula (II).

General Synthesis Scheme 3

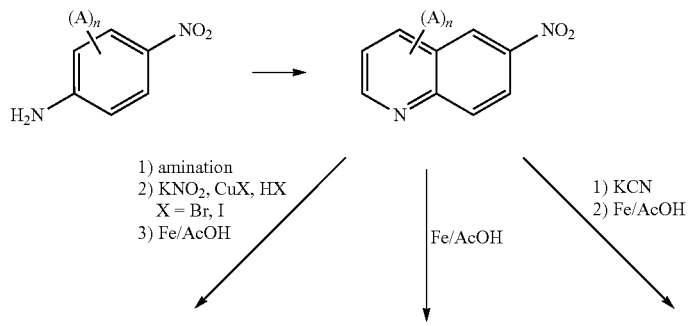

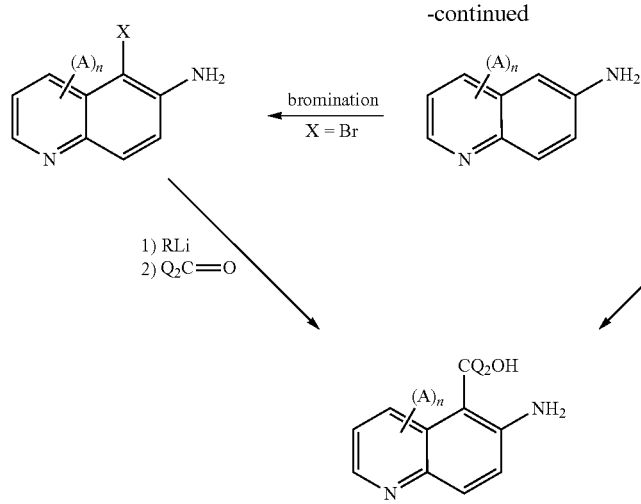
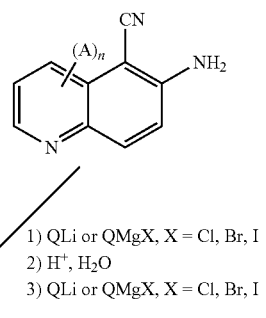

Compounds of formula (III) can be synthesized according to Scheme 3.

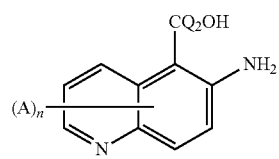

Compounds of formula (III) are prepared from 6-nitroquinolines, which can be made using the Skraup, Combes, Conrad-Limpach-Knorr, Doebner-Miller, Frieländer and Pfitzinger syntheses and their variants, as well as other routes (J. A. Joule and K. Mills, *Heterocyclic Chemistry*, 5th ed., Chichester, UK: Wiley, 2010, 188-194). In some instances, the 6-nitroquinolines are aminated with 4-amino-1,2,4-triazole, $NH_2OH·HCl$ or $Me_3N^+NH_2$. The resulting 5-amines are converted to bromides or iodides via diazonium ions, and the nitro group is reduced to an amine group. The quinolin-5-yllithium intermediates are prepared by reaction with an organolithium reagent and reaction with ketones ($Q_2C=O$) to provide compounds of formula (III). In some instances, the 6-nitroquinolines are reduced to amines and brominated with $Br_2$ or N-bromosuccinimide. In some instances, the 6-nitroquinolines are converted to 5-nitriles by reaction with KCN, followed by reduction of the nitro group to an amine group. The resulting 6-amino-5-cyanoquinolines are treated with alkyllithium or alkyl Grignard reagents and hydrolyzed with aqueous acid to provide 1-(6-aminoquinolin-5-yl)alkan-1-ones. The ketones are again treated with an alkyllithium or alkyl Grignard reagents to provide compounds of formula (III).

General Synthesis Scheme 4-1

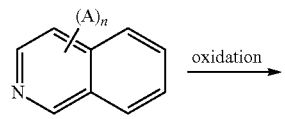

-continued

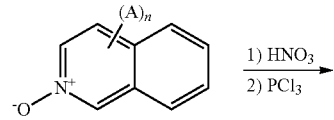
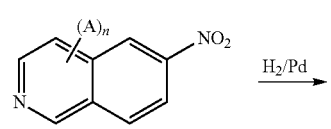
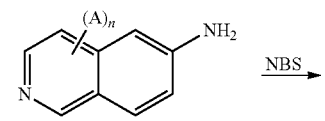
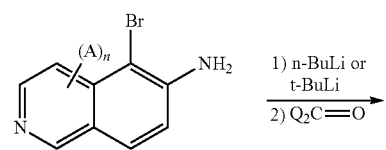
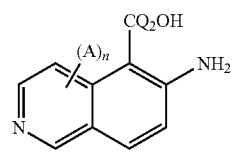

Compounds of formula (IV) can be prepared according to Scheme 4-1.

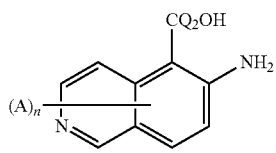
(IV)

In some instances, compounds of formula (IV) can be prepared by the Pomeranz-Fritsch synthesis, the Bischler-Napieralski synthesis, or the Pictet-Gams modification (J. A. Joule and K. Mills, *Heterocyclic Chemistry*, 5th ed., Chichester, UK: Wiley, 2010, 194-197). As shown in Scheme 4-1, isoquinolines are converted to isoquinoline-N-oxides by oxidation with $H_2O_2$ or m-chloroperbenzoic acid. The 6-nitro group is introduced by nitration with nitric acid. The N-oxides and nitro groups are simultaneously reduced with $H_2$ and Pd or $SnCl_2$, and then the compounds are brominated at the 5-position with N-bromosuccinimide (NBS). The carbinols of formula (IV) are then prepared by dehalolithiation with an alkyllithium reagent and reaction with ketones ($Q_2C=O$).

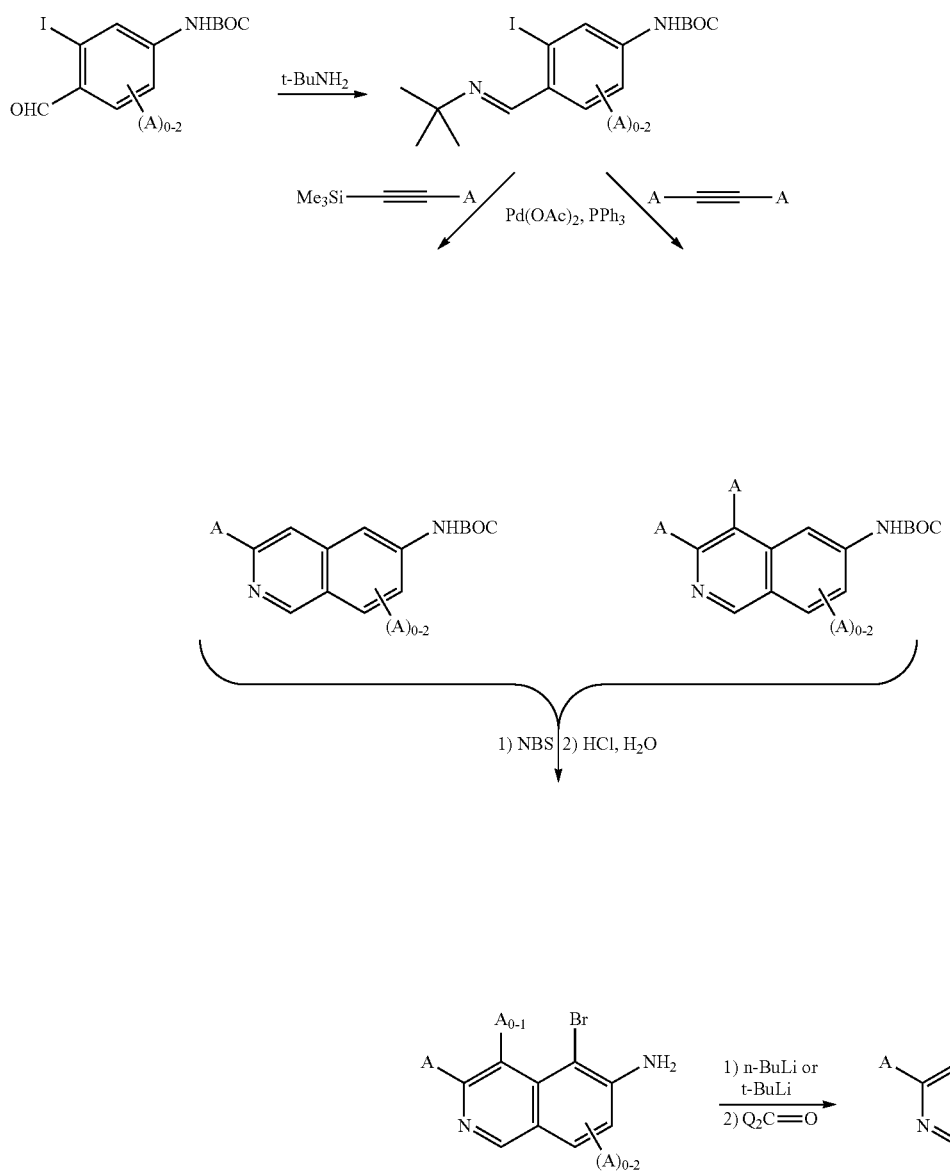

General Synthesis Scheme 4-2

As shown in Scheme 4-2, some compounds of formula (IV) are prepared from 2-iodo-4-aminobenzaldehydes (made according to the methods of J. J. Blanksma, *Chemisch Weekblad*, 6 (1911), 899-913, and R. G. R. Bacon and W. S. Lindsay, *J. Chem. Soc.*, (1958), 1375-1381), where the anilines are protected with a t-butyloxycarbonyl (BOC) group and the aldehydes are condensed with t-butylamine to form the t-butylimines. Isoquinolines with an A group in the 3-position are prepared by reaction of the 2-iodoimines with acetylenes bearing a trimethylsilyl group and an A group catalyzed by Pd(OAc)$_2$ and PPh$_3$. Isoquinolines with A groups in the 3- and 4-positions are prepared by the same Pd catalyzed reaction of the 2-iodoimines with acetylenes bearing two A groups. Isoquinolines substituted with A in the 3-position or in both the 3- and 4-positions are each independently carried forward by bromination with NBS and hydrolyzed to form the respective 6-amino-5-bromoisoquinolines, which are independently dehalolithiated with an alkyllithium reagent and allowed to react with ketones (Q$_2$C=O) to provide compounds of formula (IV).

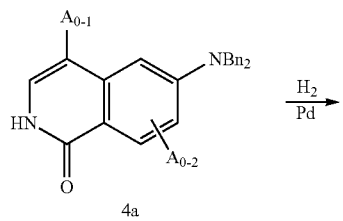

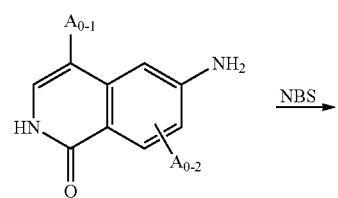

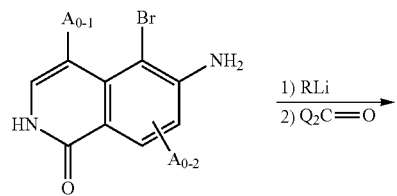

General Synthesis Scheme 4-3

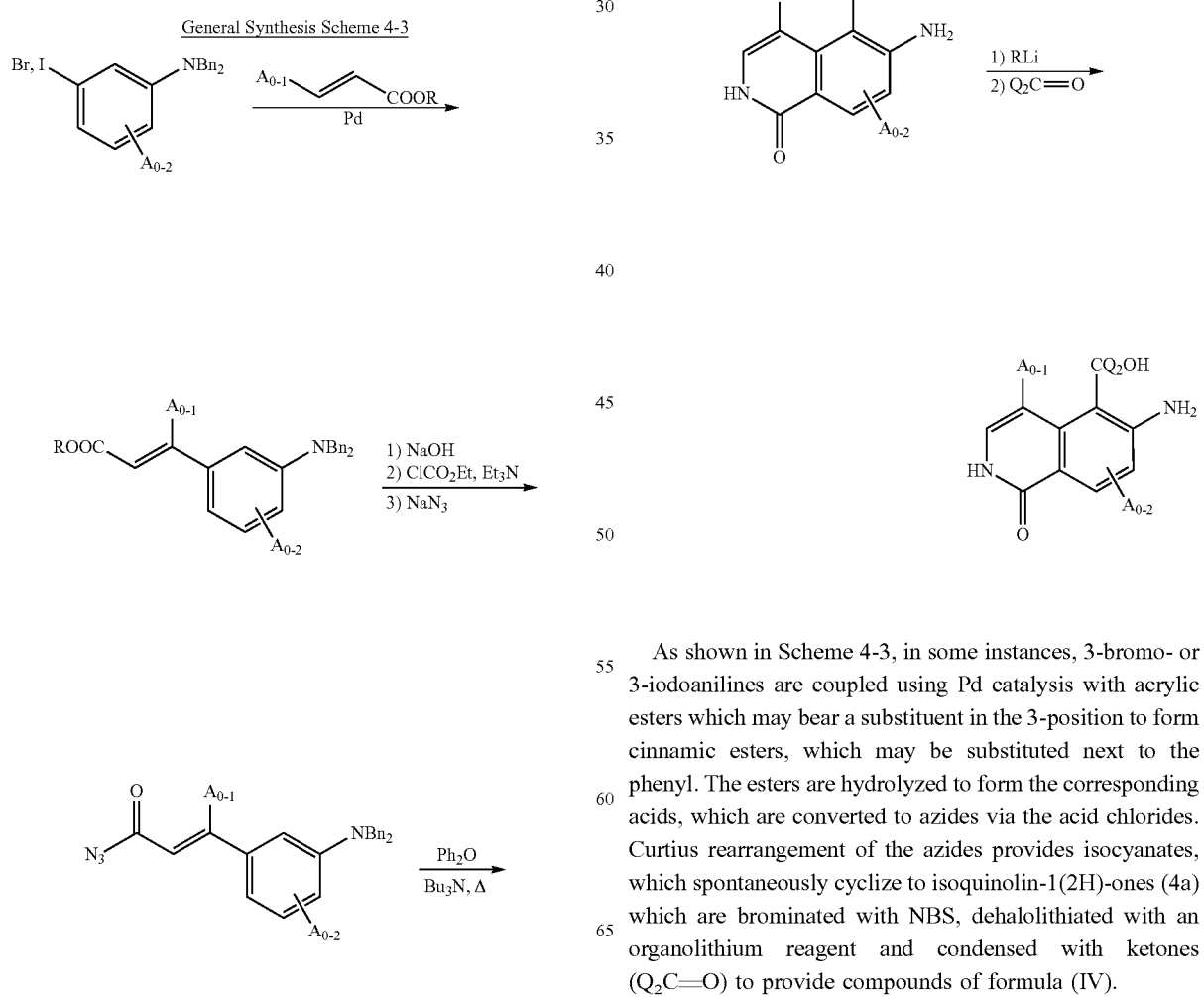

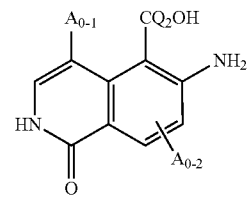

As shown in Scheme 4-3, in some instances, 3-bromo- or 3-iodoanilines are coupled using Pd catalysis with acrylic esters which may bear a substituent in the 3-position to form cinnamic esters, which may be substituted next to the phenyl. The esters are hydrolyzed to form the corresponding acids, which are converted to azides via the acid chlorides. Curtius rearrangement of the azides provides isocyanates, which spontaneously cyclize to isoquinolin-1(2H)-ones (4a) which are brominated with NBS, dehalolithiated with an organolithium reagent and condensed with ketones (Q$_2$C=O) to provide compounds of formula (IV).

General Synthesis Scheme 4-4

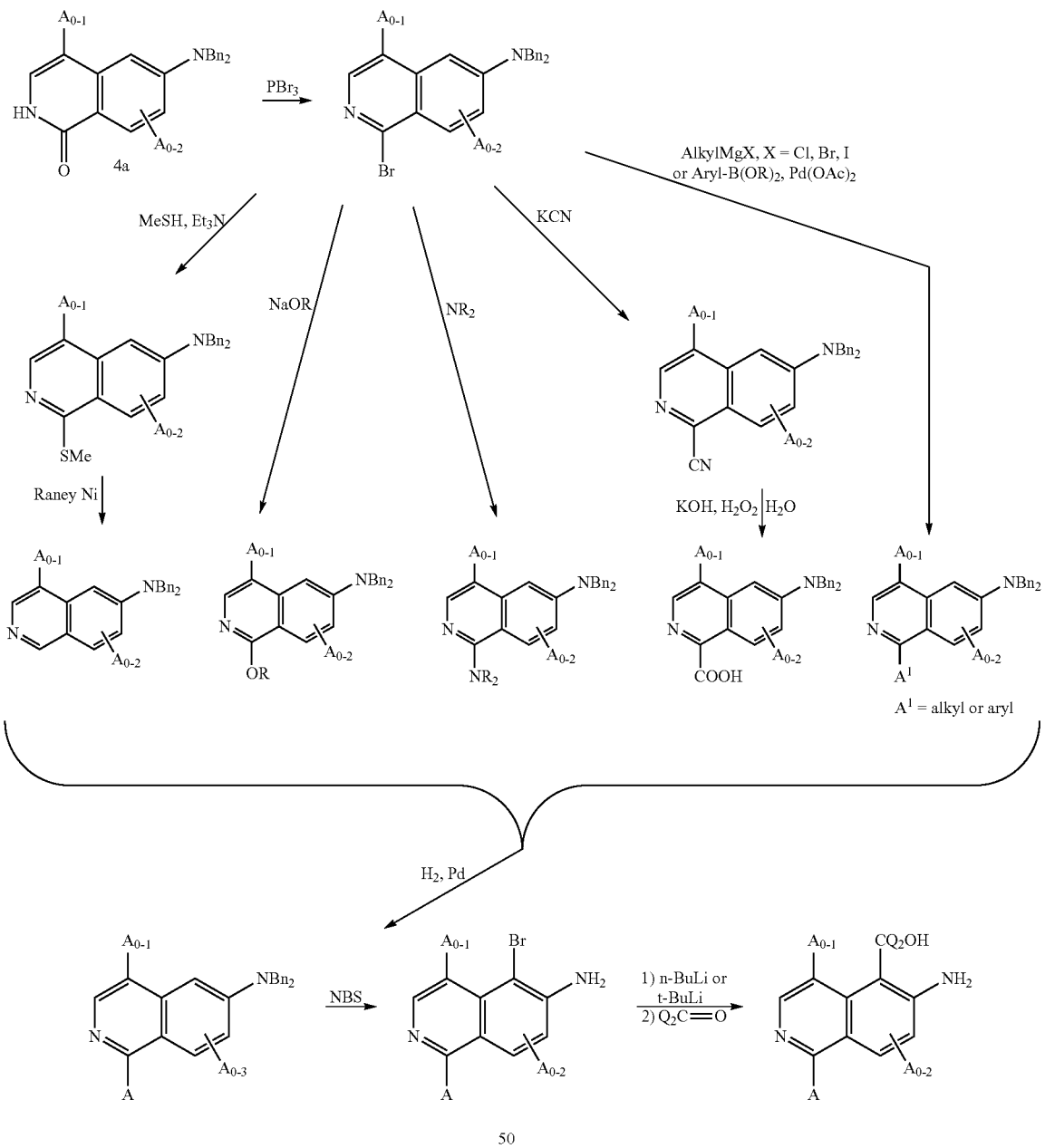

The isoquinolin-1(2H)-ones (4a) are converted to the 1-bromoisoquinolines, from which some compounds of formula (IV) are prepared as shown in Scheme 4-4. The 1-bromo substituent is removed by conversion to the thiomethyl derivative with MeSH and treatment with Raney nickel or with $H_2$ and Pd, which also deprotects the amine (not shown). Displacement of the 1-bromide with sodium alkoxides, ammonia, primary or secondary amines $NR_2$ or KCN provides the 1-alkoxy, 1-amino and 1-cyano compounds, respectively. The 1-cyanoisoquinolines are hydrolyzed to the carboxylic acids with KOH and $H_2O_2$. Alkyl substituents are introduced in the 1-position by reaction with and alkyl Grignard reagents. Aryl substituents are introduced in the 1-position by reaction with arylboronates using Pd catalysis. Each of these products is independently brominated with NBS and converted to the carbinols by dehalolithiation with an organolithium reagent and reaction with ketones ($Q_2C=O$).

General Synthesis Scheme 5-1

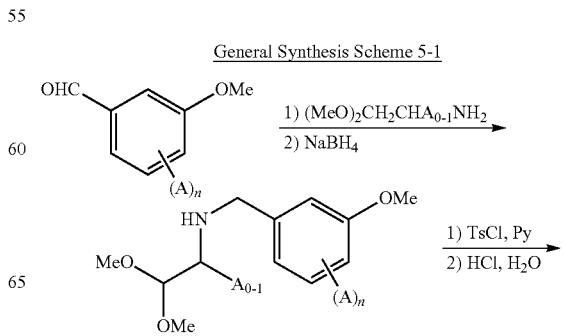

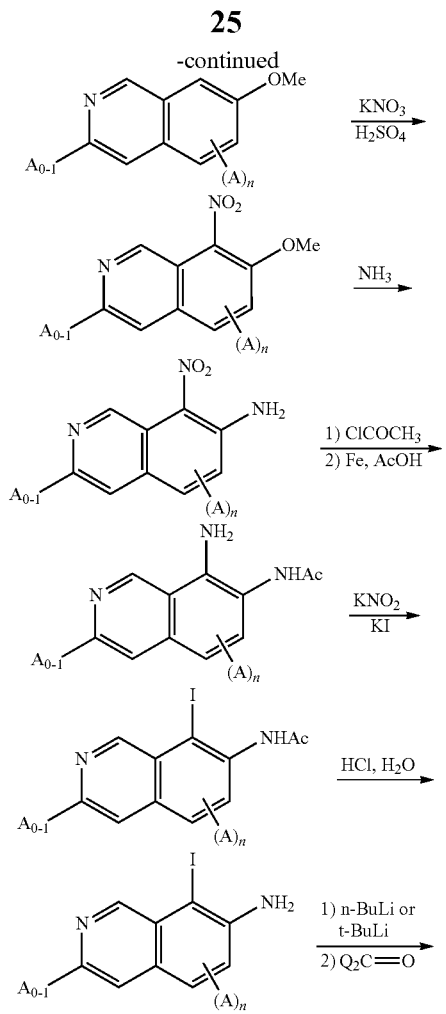

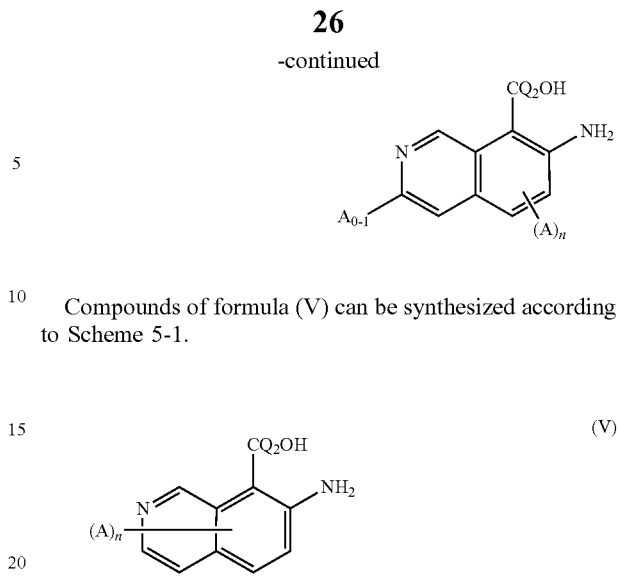

Compounds of formula (V) can be synthesized according to Scheme 5-1.

(V)

As shown in Scheme 5-1, in some pathways compounds of formula (V) are prepared by a modified Pomeranz-Fritsch synthesis wherein m-methoxybenzaldehydes are condensed with 2-aminoacetaldehyde dimethylacetals that may bear an A substituent in the 2-position, and the resulting imines are reduced to the amines with $NaBH_4$. The amines are converted to the p-toluenesulfonamides with p-toluenesulfonyl chloride (TsCl), and the isoquinolines are formed by treatment with an acid. The isoquinolines are nitrated, and the methoxy group is displaced by ammonia and the resulting amines are protected. The 8-nitro group is reduced to the amine and converted to the iodide via a diazonium salt. The remaining 7-amine is deprotected and the carbinols are formed by deiodolithiation and reaction with ketones ($Q_2C=O$).

General Synthesis Scheme 5-2

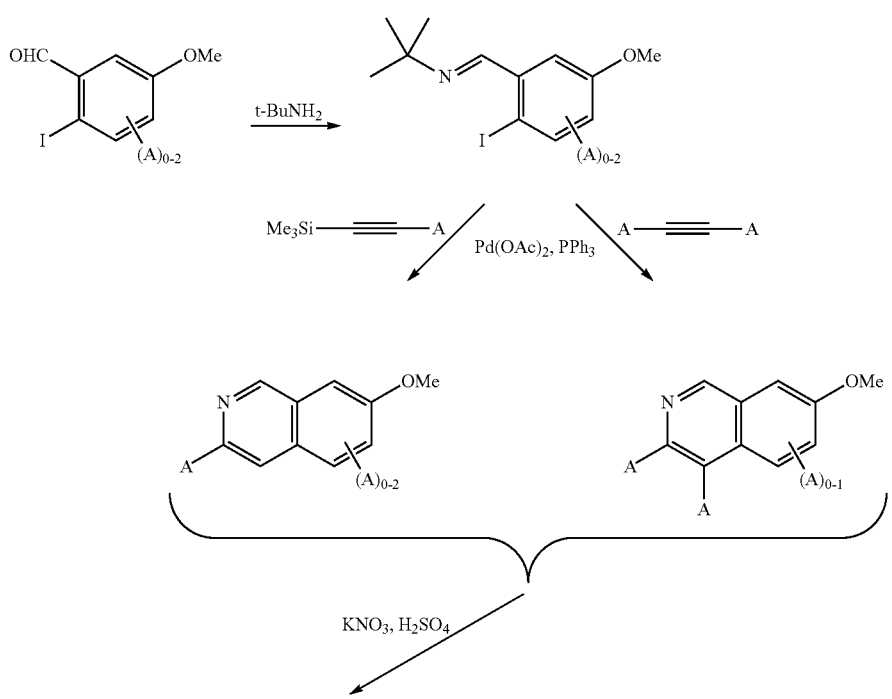

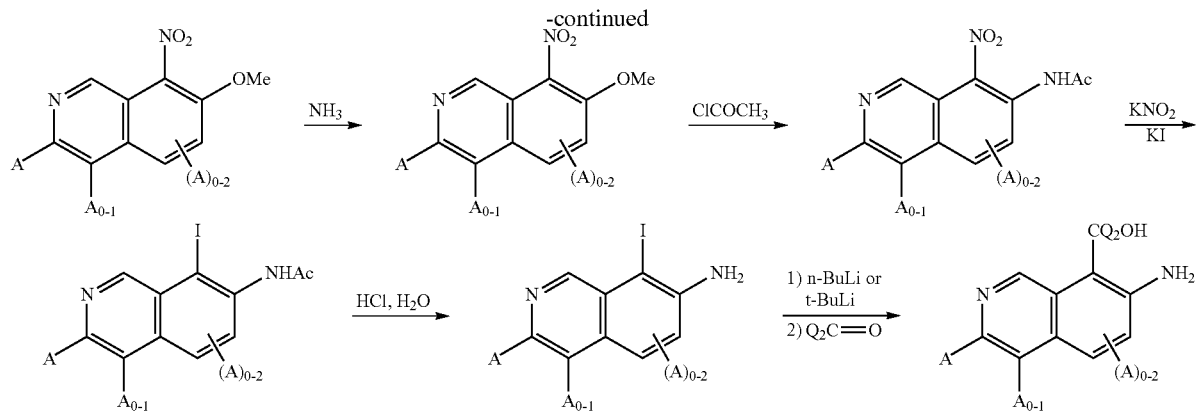

In some instances (Scheme 5-2) the compounds of formula (V) are prepared from 2-iodo-5-methoxybenzaldehydes, which are prepared using methods known in the art (e.g., E. Akguen et al., *J. Org. Chem.*, 46 (1981), 2730-2734; G. Appendino et al., *Ang. Chem., Int. Ed.*, 46 (2007), 9312-9315; S. D. Carter and T. W. Wallace, *J. Chem. Res., Synopses*, (1985), 136-7; M. Z. Cherkaoui and G. Scherowsky, *New J. Chem.*, 21 (1997), 1203-1210; D. M. Coltart and J. L. Charlton, *Can. J. Chem.*, 74 (1996), 88-94; B. Haag et al., *Org. Lett.*, 11 (2009), 4270-4273; D. C. Harrowven et al., *Tetrahedron Lett.*, 43 (2002), 7345-7347; B. A. Hathaway et al., *Syn. Comm.*, 37 (2007), 3855-3860; R. Olivera et al., *J. Org. Chem.*, 65 (2000), 6398-6411; S. Quideau et al., *Ang. Chem., Int. Ed.*, 48 (2009), 4605-4609, S4605/1-S4605/104). As in Scheme 4-1, the iodobenzaldehydes are converted to isoquinolines by condensation with t-butylamine and Pd catalyzed coupling with acetylenes, and are used to prepare the compounds of formula (V) using the same methods as in Scheme 5-1.

General Synthesis Scheme 6

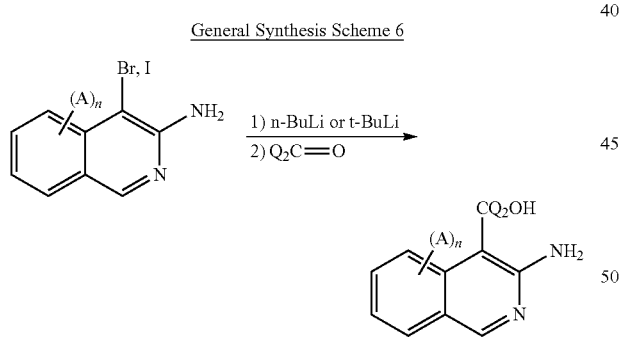

Compounds of formula (VI) can be synthesized according to Scheme 6.

(VI)

Compounds of formula (VI) are prepared from 3-amino-4-bromo- or 3-amino-4-iodoisoquinolines by dehalolithiation and reaction with ketones ($Q_2C=O$). 3-aminoisoquinolines and their 4-bromo- and 4-iodo-analogs are prepared using methods known in the art (T. Zdrojewski and A. Jonczyk, *Tetrahedron*, 51 (1995), 12439-12444; WO2007/125405; WO2003/024931; J. P. Parrish et al., *Organic Letters*, 5 (2003), 2577-2579; G. Van Baelen et al., *Tetrahedron*, 64 (2008), 11802-11809).

General Synthesis Scheme 7-1

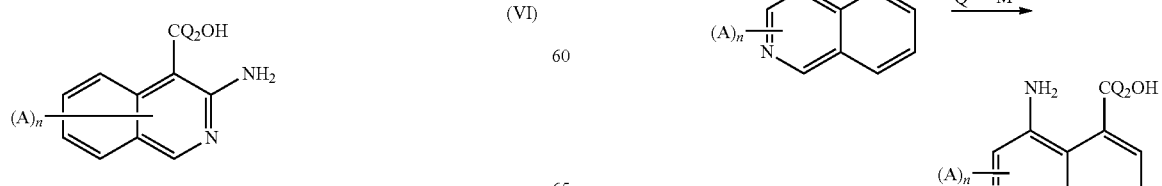

General Synthesis Scheme 7-2

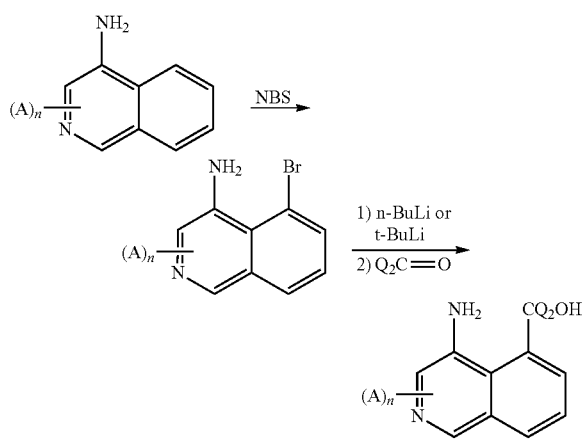

Compounds of formula (VII) can be synthesized according to Scheme 7-1.

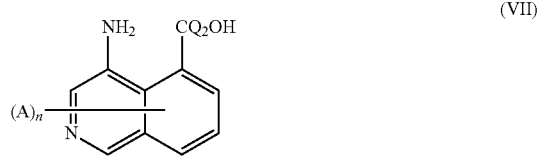

(VII)

Compounds of formula (VII) may be prepared as shown in scheme 7-1. An optionally substituted 4-aminoisoquinoline is acetylated with acetic anhydride, and the amido product is then acylated at the 5-position by action of a Lewis acid catalyst such as aluminum chloride. Then the acetyl amido group is hydrolyzed with a base such as lithium hydroxide and the resulting carbonyl is reacted with a Grignard or organolithium reagent to yield the final product. Alternatively, compounds of formula (VII) can be prepared by bromination of 4-aminoisoquinoline as shown in Scheme 7-2. Bromination can be directed to the 5-position using a Lewis acid catalyst such as aluminum chloride (see, e.g., M. Gordon, D. E. Pearson, *J. Org Chem.*, 29 (1964) 329-332). Halogen metal exchange followed by reaction with the appropriate carbonyl yields the product compound. Depending on the specific substituent A, the route will be chosen that is most appropriate. For example, when A is halogen, then Scheme 7-1 is preferred, as selective metal halogen exchange for the 5-bromo versus the A-substituent could be problematic. There are a variety of substituted 4-aminoisoquinolines that are commercially available (e.g., methyl, Cl, Br, MeO) and can be funneled into one pathway or the other. 4-aminoisoquinolines are typically made by bromination of the isoquinoline at the 4-position and conversion of the bromo group to the amine functionality with either ammonia or metal amide (see, e.g., B. K. Kulkarni et al., Indian Pat. Appl., 2005MU00436, published 6 Jul. 2007 and PCT publication WO 2007/109365, published 27 Sep. 2007).

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. For example, $C_{1-6}$ alkyl is intended to include $C_1$, $C_2$, $C_3$, $C_4$, $C_5$ and $C_6$ alkyl groups. Examples of alkyl groups include methyl, ethyl, n-propyl, isopropyl, n-butyl, iso-, sec- and tert-butyl, pentyl, hexyl and the like. It should be understood that when alkyl is methyl, deuteromethyl is also included within the scope of the invention.

"Cycloalkyl", "cyclic alkyl" or "carbocycle" means a saturated carbocyclic ring having a specified number of carbons, e.g., $C_{3-6}$-cycloalkyl is a ring containing 3 to 6 carbons, including cyclopropyl, cyclobutyl, cyclopentyl and cyclohexyl.

"Halogen" includes fluorine, chlorine, bromine and iodine.

"Carbinol" is a substituted methanol functionality.

Compounds within the scope of the instant invention may contain chiral centers and thus are capable of existing as racemates, racemic mixtures, diastereomers and single enantiomers. All such forms should be understood as within the scope of this invention.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

The term "pharmaceutically acceptable salts" is art-recognized, and includes relatively non-toxic, inorganic and organic acid addition salts of compositions, including without limitation, the compounds of the invention, excipients, carriers and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci. 66:1-19 (1977).

The compounds of the instant invention may be administered in the parent form or as a pharmaceutically acceptable salt. The term compound of the invention should be understood to include both. Pharmaceutically acceptable salts can be prepared from a parent compound that contains basic or acidic moieties by conventional chemical methods. Acid addition salts would include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For reviews on pharmaceutically acceptable salts, see S. M. Berge, L. D. Bighley and D. C. Monkhouse, *Pharmaceutical Salts, J. Pharm. Sci.*, 66 (1977), 1-19 and P. H. Stahl and C. G. Wermuth (eds.), *Pharmaceutical Salts: Properties, Selection, and Use*, Weinheim, Germany: Wiley and Zürich: Verlag Helvetica Chimica Acta, 2002 [ISBN 3-906390-26-8], incorporated herein by reference. Reference to the parent compound or a salt thereof should be understood to include all hydrates of the compound and all polymorphic forms of the parent compound.

A "patient," "subject," or "host" to be treated by the subject method may mean either a human or non-human animal, such as primates, mammals, and vertebrates.

The present invention provides compounds, compositions and methods for treating, reducing a symptom of and reducing the risk of a retinal disease or disorder in which accumulation of A2E and/or lipofuscin in retinal tissue or VEGF signaling by RPE cells in response to oxidative stress is involved. For examples, the present invention provides compounds, compositions and methods for treating, reducing a symptom of and reducing the risk of macular degeneration or other retinal diseases or disorders caused by accumulation of A2E and/or lipofuscin in retinal tissue or by VEGF signaling by RPE cells in response to oxidative stress. Specifically the compounds are useful in treating all forms of macular degeneration, including dry AMD, GA secondary to dry AMD, wet AMD and Stargardt's disease. The fundamental cause of all such forms of the disease is believed to be the cytotoxicity that results from the accumulation of A2E and lipofuscin inside RPE cells which causes lysosomal failure and oxidative stress. This in turn triggers the apoptosis of GA, VEGF signaling in RPE cells which leads to the choroidal neovascularization of wet AMD, and the formation of drusen whose A2E-oxirane derivatives trigger complement activation. A2E synthesis and accumulation can be reduced pharmacologically, which in turn treats or lowers the risk of macular degeneration, including dry AMD and other forms of macular degeneration, by limiting the amount of RAL available for reaction with PE, which is the first step in the A2E biosynthetic pathway, and the progression from dry AMD to GA and wet AMD. In the PCT publication WO 2006/127945, compounds are described as reducing RAL concentrations in photoreceptor outer segments by chemically reacting irreversibly with RAL and thus are useful in treating or lowering the risk of macular degeneration in a patient. The compounds of the instant invention show more favorable reaction energetics in the formation of the RAL-drug end product and thus may have even greater potency in treating or lowering the risk of macular degeneration.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease, disorder or condition includes ameliorating at least one symptom of the particular disease, disorder or condition, even if the underlying pathophysiology is not affected.

The term "preventing" is art-recognized and includes stopping a disease, disorder or condition from occurring in a subject which may be predisposed to the disease, disorder and/or condition but has not yet been diagnosed as having it. Preventing a condition related to a disease includes stopping the condition from occurring after the disease has been diagnosed but before the condition has been diagnosed.

The term "reducing the risk of" means that the likelihood of a subject to suffer from a disease, disorder or condition is decreased, for example, from between 50% and 100% to between 0 and 90%, between 0 and 80%, between 0 and 70%, between 0 and 60%, or between 0 and 50%, or decreased by 10%, 20%, 30%, 40%, 50%, 60%, 70%, 80%, or 90%.

The present invention is also directed to manufacture of a medicament for treating, reducing a symptom of or reducing the risk of developing a retinal disease or disorder in which accumulation of A2E and/or lipofuscin in retinal tissue or VEGF signaling by RPE cells in response to oxidative stress is involved in a subject in need thereof, wherein the composition comprises a compound of the invention or a pharmaceutically acceptable salt thereof. In one illustration, the present invention is directed to a method for the manufacture of a medicament for the treatment, reduction of a symptom of or reduction of risk of macular degeneration in a patient. More specifically, this aspect of the invention is directed to the manufacture of a medicament for the treatment or reduction of risk of macular degeneration disease in a patient, including dry AMD, GA secondary to dry AMD, wet AMD and Stargardt's disease.

The present invention is also directed to a composition for use in a method for treating, reducing a symptom of or reducing the risk of developing a retinal disease or disorder in which accumulation of A2E and/or lipofuscin in retinal tissue or VEGF signaling by RPE cells in response to oxidative stress is involved in a subject in need thereof, wherein the composition comprises a compound of the invention or a pharmaceutically acceptable salt thereof. In one illustration, the invention is directed to a composition for use in a method for treating, reducing a symptom of or reducing the risk of developing macular degeneration. More specifically, this aspect of the invention is directed to a composition for use in a method for treating, reducing a symptom of or reducing the risk of developing in a patient, including dry AMD, GA secondary to dry AMD, wet AMD and Stargardt's disease.

The compounds of the invention may be administered with a pharmaceutically acceptable carrier in a pharmaceutical composition. The pharmaceutical compositions of the present invention encompass any composition made by admixing a therapeutically effective amount of a compound of the invention with a pharmaceutically acceptable carrier. The administration may be by oral, parenteral, topical or intra-ocular means. Topical administration may be in the form of drops or controlled release topical formulations including films and adhesives. Intra-ocular administration may take the form of subconjunctival, subtenon's capsule, retrobulbar or intravitreal injections, depots or implants. Compounds administered by these routes may be in solution or suspension form. Administration of compounds by depot injection may contain pharmaceutically acceptable carriers or excipients, which may be natural or synthetic, biodegradable or non-biodegradable, and may facilitate drug release in a controlled manner. Implants used for controlled release of a compound may be composed of natural or synthetic, biodegradable or non-biodegradable materials. The carrier is acceptable in that it is compatible with the other components of the composition and is not injurious to the patient. Some examples of carriers include (1) sugars such as lactose glucose and sucrose, (2) starches such as corn starch and potato starch, (3) cellulose and (4) cyclodextrins. A useful topical formulation is described in the PCT publication WO 2011/072141, the contents of which are herein incorporated by reference.

In one exemplification, the pharmaceutical compositions of the present invention encompass a composition made by admixing a therapeutically effective amount of a compound of the invention with an oligomeric or a polymeric carrier such as a cyclodextrin, or chemically modified cyclodextrin, including trimethyl-β-cyclodextrin, 2-hydroxyethyl-(3-β-cyclodextrin, 2-hydroxypropyl-β-cyclodextrin, 3-hydroxypropyl-β-cyclodextrin, and β-cyclodextrin sulfobutylether sodium salt (or potassium salt). Exemplifying an oligomeric or a polymeric carrier is β-cyclodextrin sulfobutylether sodium salt. The amount of β-cyclodextrin sulfobutylether sodium salt in the composition may range from about 0.01% to 30% weight/volume. In one illustration, the concentration of β-cyclodextrin sulfobutylether sodium salt is 5-25% weight/volume. Further illustrating the concentration of β-cyclodextrin sulfobutylether sodium salt is 6-20% weight/volume. In one exemplification the concentration of β-cyclodextrin sulfobutylether is 6-12% weight/volume. Further exemplifying the concentration of β-cyclodextrin sulfobutylether is 9-10% weight/volume, including 9.5% weight/volume. The amount of the compound of the invention in the composition may range 0.01-20%, 0.02-15%, 0.04-10%, 0.06-5%, 0.08-1%, or 0.09-0.5% (weight/volume). More particularly, the composition may contain a compound of the invention at a concentration of 0.09-0.5% (weight/volume), such as 0.1%. Efficacious levels of the composition comprising a compound of the invention and a cyclodextrin can be delivered to the back of the eye and specifically to the RPE and retina. The composition may further comprise saline and may be buffered with, for example, a phosphate buffer, so that the pH of the composition is brought to a pH range of 5.5-8.5 or, more particularly, a pH range of 6.5-7.5. A preservative may optionally be included in the composition. Such preservatives can include both chemical stabilizers, such as an anti-oxidant, and antiseptics.

In an eye drop formulation the composition may contain the active compound at a concentration of 0.01-20%, 0.02-15%, 0.04-10%, 0.06-5%, 0.08-1%, or 0.09-0.5% (weight/volume). More particularly, the eye drop formulation contains a compound of the invention at a concentration of 0.09-0.5% (weight/volume), such as 0.1%.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. A therapeutically effective dose, of a compound of the invention in an oral formulation, may vary from 0.01 mg/kg to 50 mg/kg patient body weight per day, more particularly 0.01 to 10 mg/kg, which can be administered in single or multiple doses per day. For oral administration the drug can be delivered in the form of tablets or capsules containing 1 mg to 500 mg of the active ingredient specifically, 1 mg, 5 mg, 10 mg, 20 mg, 50 mg, 100 mg, 250 mg, and 500 mg, or in the forms of tables or capsules containing at least 1%, 2%, 5%, 10%, 15%, 20%, 25%, 30%, 40%, 50% (w/w) of the active ingredient. For example, the capsules may contain 50 mg of the active ingredient, or 5-10% (w/w) of the active ingredient. For example, the tablets may contain 100 mg of the active ingredient, or 20-50% (w/w) of the active ingredient. For example, the tablet may contain, in addition to the active ingredient, a disintegrant (e.g., croscarmellose or its sodium salt and methyl cellulose), a diluent (e.g., microcrystalline cellulose), and a lubricant (e.g., sodium stearate and magnesium stearate). The drug can be administered on a daily basis either once, twice or more per day.

Parenteral formulations comprising a compound of the invention can be prepared in aqueous isotonic solutions or suspensions, and suppositories are advantageously prepared from fatty emulsions or suspensions. The formulations may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional methods, and may contain about 0.1 to 75%, preferably about 1 to 50%, of a compound of the invention.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

A "pharmaceutical composition" is a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, parenteral, topical, intra-ocular, and the like. Dosage forms for topical administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and optionally with any preservatives, buffers, or propellants that may be required.

The compounds of the invention are provided in therapeutic compositions. The compound is present in an amount that is therapeutically effective, which varies widely depending largely on the particular compound being used. The preparation of pharmaceutical or pharmacological compositions will be known to those of skill in the art in light of the present disclosure.

The terms "administering of" or "administering a" should be understood to mean providing a compound of the invention or a prodrug thereof to a patient in need of treatment or reduction in risk.

Upon formulation, therapeutics will be administered in a manner compatible with the dosage formulation, and in such amount as is pharmacologically effective. The formulations are easily administered in a variety of dosage forms, such as the forms described above.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. The amount of compound incorporated into the composition also depends upon the desired release profile, the concentration of the compound required for a biological effect, and the length of time that the biologically active substance has to be released for treatment. In certain embodiments, the biologically active substance may be blended with a polymer matrix at different loading levels, in one embodiment at room temperature and without the need for an organic solvent. In other embodiments, the compositions may be formulated as microspheres. In some embodiments, the compound may be formulated for sustained release.

For oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, croscarmellose or its sodium salt, and the like. Diluents, include, e.g., lactose, dextrose, sucrose, mannitol, sorbitol, cellulose and/or glycine.

The compounds of the invention can also be administered in such oral dosage forms as timed release and sustained release tablets or capsules, pills, powders, granules, elixers, tinctures, suspensions, syrups and emulsions.

The compounds of the invention can also be administered topically, such as directly to the eye, e.g., as an eye-drop or ophthalmic ointment. Eye drops typically comprise an effective amount of at least one compound of the invention and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, 1985, Trans Ophthalmol Soc U K 104(Pt 4): 402-9; Ashton et al., 1991, J Pharmacol Exp Ther 259(2): 719-24; Green et al., 1971, Am J Ophthalmol 72(5): 897-905). The most commonly used penetration enhancer is benzalkonium chloride (Tang et al., 1994, J Pharm Sci 83(1): 85-90; Burstein et al, 1980, Invest Ophthalmol Vis Sci 19(3): 308-13), which also works as preservative against microbial contamination.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

EXAMPLES

Example 1

Synthesis of 2-(3-amino-6-chloro-5-fluoroquinolin-4-yl)propan-2-ol (1)

(E)- and (Z)-3-chloro-2-fluoro-6-(2-nitrovinylamino)benzoic acid (1-1). 37.19 g crude wet methazonic acid (prepared by the method of G. B. Bachman et al., *J. Am. Chem. Soc.* 69 1947, 365-371) was mixed with 50 g 6-amino-3-chloro-2-fluorobenzoic acid (Butt Park Ltd., Camelford, Cornwall, UK) and 750 mL acetone and shaken until a clear solution was formed. To it was added sequentially 200 mL water and 200 mL 12 N HCl, and the solution was kept 3 days at room temperature. The mixture was diluted with 2 L water and filtered. The filtrate was evaporated to remove acetone and filtered. The combined solids were washed with water (4×200 mL) and dried at 60° C. under high vacuum to afford 1-1 as a 4.5:1 mixture of E- and Z-isomers.

$^1$H NMR (400 MHz, DMSO-$d_6$) δ: E-isomer 6.79 (d, 1H, J=6.4 Hz), 7.58 (d, 1H, J=8.4 Hz), 7.83 (t, 1H, J=8.4 Hz), 7.99 (dd, 1H, J=6.4, 13.2 Hz), 12.34 (d, 1H, NH, J=13.2 Hz), 14.52 (br, 1H, OH).

Z-isomer 7.39 (d, 1H, J=11.2 Hz), 7.42 (d, 1H, J=9.6 Hz), 7.71 (t, 1H, J=8.4 Hz), 8.49 (t, 1H, J=11.6 Hz), 10.24 (d, 1H, NH, J=12.4 Hz), 14.52 (br, 1H, OH).

LC-MS: 259 [(M-H)$^-$].

6-chloro-5-fluoro-3-nitroquinolin-4-ol (1-2). A mixture of 62.0 g (1-1), 55.2 g N-ethyl-N'-(3-dimethylaminopropyl) carbodiimide hydrochloride (EDC) and 30.1 g N-hydroxysuccinimide (HOSu) in 1 L absolute dimethylformamide (DMF) was stirred at room temperature for 1 h. 4-dimethylaminopyridine (DMAP, 38.7 g) was added and the mixture was stirred at room temperature for 2 h. The mixture was filtered, and the solid was washed with 10% HOAc (4×200 mL), air-dried overnight, and then dried at 60° C. under high vacuum to give (1-2) as a pale yellow powder.

$^1$H NMR (400 MHz, DMSO-$d_6$) δ: 7.52 (dd, 1H, J=0.8, 8.8 Hz), 7.91 (dd, 1H, J=7.2, 8.8 Hz), 9.15 (s, 1H), 13.0 (br, 1H, OH).

LC-MS: 242.9 (MH)$^+$, 264.9 (MNa)$^+$.

4-bromo-6-chloro-5-fluoro-3-nitroquinoline (1-3). A mixture of 40 g (1-2) and 71 g POBr$_3$ in 150 mL dry DMF was stirred at 80° C. for 1 h. The mixture was cooled to room temperature, diluted with 2 L CH$_2$Cl$_2$, and transferred to a separatory funnel containing 1.5 L ice water. The organic layer was separated, washed with ice water (3×1.5 L), dried with MgSO$_4$, and evaporated to give crude (1-3) as a light brown solid, which was used without further purification.

$^1$H NMR (400 MHz, CDCl$_3$) δ: 4.70 (br, 2H, NH$_2$), 7.42 (dd, 1H, J=6.0, 9.0 Hz), 7.73 (dd, 1H, J=1.8, 8.8 Hz).

LC-MS: 274.8 (MH)$^+$, 276.8 [(M+2)H]$^+$, 278.8 [(M+4)H]$^+$.

4-bromo-6-chloro-5-fluoroquinolin-3-amine (1-4). Crude (1-3) (51.2 g) was dissolved in 40 mL glacial HOAc under Ar, 3 g Fe powder was added, and the mixture was stirred at 60° C. for 10 min. The mixture was diluted with 200 mL EtOAc, filtered through Celite, and the Celite was washed thoroughly with EtOAc. The combined filtrates were passed through a short silica gel column, and the column was washed with EtOAc until all (1-4) was recovered. The combined EtOAc fractions were evaporated to dryness to give crude (1-4) which was crystallized from hexanes-EtOAc to provide (1-4) as a pale brown solid.

$^1$H NMR (400 MHz, CDCl$_3$) δ: 4.70 (br, 2H, NH$_2$), 7.42 (dd, 1H, J=6.0, 9.0 Hz), 7.73 (dd, 1H, J=1.8, 8.8 Hz).

LC-MS: 274.8 (MH)$^+$, 276.8 [(M+2)H]$^+$, 278.8 [(M+4)H]$^+$.

2-(3-amino-6-chloro-5-fluoroquinolin-4-yl)propan-2-ol (1). A dry 1 L round bottom flask was flushed with argon and cooled to −78° C. in a dry ice/acetone bath. Dry tetrahydrofuran (THF, 300 mL) was injected, followed by 72.6 mL 2.5 M n-BuLi/hexanes. (1-4) (20 g) in 300 mL dry THF was added dropwise with vigorous stirring over 2 h, affording a dark red solution of the 4-quinolinelithium. Ultra dry acetone (27 mL) was added dropwise over 10 min, and the solution was stirred for an additional 10 min. A solution of 20 g NH$_4$Cl in 100 mL water was added and the mixture was warmed to room temperature, transferred to a separatory funnel containing 300 mL EtOAc, and shaken thoroughly. The organic layer was separated and the aqueous layer was extracted with EtOAc (2×250 mL). The combined organic layers were dried with anhydrous MgSO$_4$ and evaporated to a dark brown residue which was partially purified by chromatography on a silica gel column eluted with hexanes-EtOAc to afford a mixture containing 6-chloro-5-fluoroquinolin-3-amine and (1). (1) was isolated by crystallization from hexanes-EtOAc.

$^1$H NMR (400 MHz, CD$_3$OD) δ: 1.79 (s, 3H), 1.80 (s, 3H), 7.36 (dd, 1H, J=7.2, 8.8 Hz), 7.61 (dd, 1H, J=1.6, 9.0 Hz), 8.35 (s, 1H).

$^{13}$C NMR (100 MHz, CD$_3$OD) δ: 29.8, 29.9, 76.7, 120.4 (d, $J_{C-F}$=12 Hz), 120.5 (d, $J_{C-F}$=4 Hz), 125.4, 126.1 (d, $J_{C-F}$=3 Hz), 126.6 (d, $J_{C-F}$=3 Hz), 143.1, 143.2 (d, $J_{C-F}$=5 Hz), 148.3, 152.7 (d, $J_{C-F}$=248 Hz).

LC-MS: 254.9 (MH)$^+$, 256.9 [(M+2)H]$^+$.

Example 2

Synthesis of 2-(3-amino-6-chloroquinolin-4-yl)propan-2-ol (2)

6-chloro-3-nitroquinolin-4-ol (2-1). A mixture of cis- and trans-5-chloro-2-(2-nitrovinylamino)benzoic acid (68.4 g, O. Sus et al., *Liebigs Ann. Chem.* 583 1953, 150-160), 73 g EDC and 35.7 g HOSu in 1 L dry DMF was stirred at room temperature for 1 h. After adding 45.8 g DMAP the mixture was stirred at room temperature for 2 h. To the stirred mixture was slowly added 1 L 10% HOAc, and the resulting suspension was poured into 2 L 10% HOAc. The solid was filtered off, washed with 10% HOAc (4×400 mL) and dried at 80° C. under high vacuum to give (2-1) as a tan powder.

4-bromo-6-chloro-quinolin-3-amine (2-2). A mixture of 25 g (2-1) and 50 g POBr$_3$ in 100 mL dry DMF was stirred at 80° C. for 1 h. The reaction mixture was cooled to room temperature, diluted with 2 L CH$_2$Cl$_2$, and transferred to a separatory funnel containing 1 L ice water. The organic layer was separated, washed with ice water (3×1 L), dried with MgSO$_4$, and evaporated to provide crude 4-bromo-6-chloroquinolin-4-ol as a light brown solid (38 g, 100% crude yield). The quinolinol was dissolved in 750 mL glacial HOAc, 36 g iron powder was added, and the stirred mixture was heated under Ar at 60° C. until the color turned to grey. The mixture was diluted with 2 L EtOAc, filtered through Celite, and the Celite was washed with EtOAc. The combined filtrates were passed through a short silica gel column which was washed with EtOAc until all (2-2) was recovered. The combined fractions were evaporated to dryness and the residue was crystallized from hexanes-EtOAc to provide (2-2) as a tan solid.

$^1$H NMR (400 MHz, CDCl$_3$) δ: 4.47 (br, 2H, NH$_2$), 7.41 (dd, 1H, J=2.4, 8.8 Hz), 7.89 (d, 1H, J=9.2 Hz), 7.96 (d, 1H, J=2.4 Hz), 8.45 (s, 1H).

LC-MS: 256.7 (MH)$^+$, 258.7 [(M+2)H]$^+$, 260.7 [(M+4)H]$^+$.

Synthesis of 2-(3-amino-6-chloroquinolin-4-yl)propan-2-ol (2). A mixture of 20 g (2-2) and 800 mL dioxane was stirred at 60° C. until a solution formed, cooled to room temperature, and sparged with dry HCl for 5 min. The solvent was evaporated, 500 mL dioxane was added and evaporated to provide 4-bromo-6-chloroquinolin-3-aminium hydrochloride. The product was mixed with 100 g NaI and 600 mL dry MeCN and refluxed overnight. The solvent was evaporated and the residue was partitioned between 500 mL EtOAc and a solution of 10 g NaHCO$_3$ in 500 mL water. The organic layer was separated, and the aqueous layer was extracted with EtOAc (2×200 mL). The combined organic layers were dried with MgSO$_4$ and evaporated to provide 6-chloro-4-iodoquinolin-3-amine as a tan solid. A dry 1 L round bottom flask was flushed with Ar and cooled to −78° C. in a dry ice/acetone bath. Dry THF (350 mL) was added followed by 188 mL 1.7 M t-BuLi/pentane with vigorous stirring. A solution of 25.8 g crude 6-chloro-4-iodoquinolin-3-amine in 350 mL dry THF was added dropwise to the stirred mixture. When addition was complete the reaction mixture was stirred at −78° C. for 5 min. Ultra dry acetone (50 mL) was added dropwise and the solution was stirred at −78° C. for 10 min after addition was complete. A solution of 20 g NH$_4$Cl in 200 mL water was added and the mixture was warmed up to room temperature, transferred to a separatory funnel containing 300 mL EtOAc. The organic layer was separated and the aqueous layer extracted with EtOAc (2×250 mL). The combined organic layers were dried with MgSO$_4$ and evaporated to a dark brown residue. The residue was partially purified by column chromatography on silica gel eluted with hexanes-EtOAc. All fractions containing (2-3) were combined and evaporated to give crude (2-3) as a red oil.

A batch of crude (2) (ca. 2 g) obtained from a separate synthesis was added to this product, and the combined batches were dissolved in 50 mL EtOAc and filtered. The filtrate and washings were combined and concentrated to an oil which was diluted with 10 mL hot hexanes, treated dropwise with EtOAc until a clear solution formed, and allowed to evaporate at room temperature overnight in the fume hood. The oily mother liquor was removed and the solid was washed with minimum volumes of 3:1 hexanes-EtOAc. After recrystallization twice from hexanes-EtOAc, a first crop of pure (2) was obtained as off-white crystals. All the mother liquor and washings were pooled and EtOAc (ca. 50 mL) was added to form a clear solution which was extracted with 0.5 N aq. HCl (4×100 mL). The aqueous layers were pooled and neutralized with 20% NaOH to pH 8. The resulting suspension was extracted with EtOAc (3×50 mL) and the combined organic layers were dried with MgSO$_4$ and evaporated to dryness. The residue was purified by column chromatography and two crystallizations from hexanes-EtOAc to provide a second crop of (2-3). A third crop (2-3) was obtained by fractional crystallization of the combined mother liquor and washings from hexanes-EtOAc.

$^1$H NMR (400 MHz, CDCl$_3$) δ: 1.93 (s, 6H), 3.21 (br, 1H, OH), 5.39 (br, 2H, NH$_2$), 7.29 (dd, 1H, J=2.0, 8.8 Hz), 7.83 (d, 1H, J=8.8 Hz), 7.90 (d, 1H, J=2.0 Hz), 8.21 (s, 1H).

$^{13}$C NMR (100 MHz, CDCl$_3$) δ: 31.5, 76.5, 123.2, 124.6, 125.7, 127.5, 131.5, 131.9, 138.8, 141.5, 146.5.

LC-MS: 236.9 (MH)$^+$, 238.9 [(M+2)H]$^+$.

Example 3

In Vitro Evaluation of Representative Compounds of the Invention

Definition of Parameters.

The parameters associated with the analysis of RAL depletion kinetics are as follows:

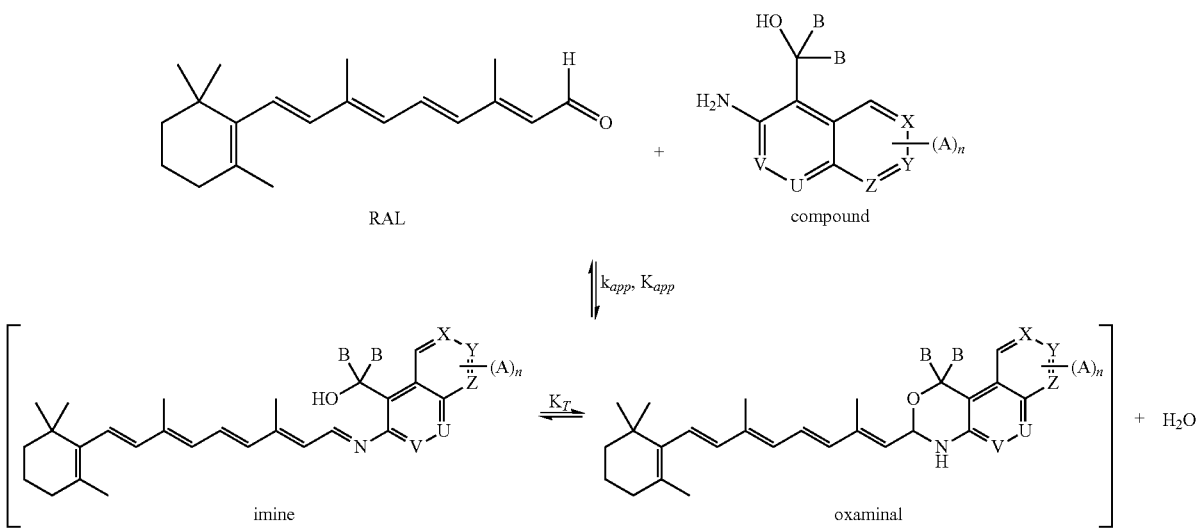

$k_{app}$: apparent second order rate constant of RAL depletion by drug.

$K_{app}$: apparent equilibrium constant of RAL depletion by drug.

$$K_{app} = \frac{([imine] + [oxaminal])[H_2O]}{[RAL][drug]} \quad (1)$$

$\Delta G_{app}$: apparent free energy change of RAL depletion by drug.

$$\Delta G_{app} = -RT \ln K_{app} \quad (2)$$

$K_T$: equilibrium constant of tautomerism from imine (ring opened) to oxaminal (ring closed).

$$K_T = \frac{[oxaminal]}{[imine]} \quad (3)$$

$\Delta G_T$: free energy change of tautomerism from imine to oxaminal.

$$\Delta G_T = -RT \ln K_T \quad (4)$$

General Methods.

Determination of $k_{app}$, $K_{app}$ and $\Delta G_{app}$ in rod outer segments. Frozen bovine rod outer segment preparation (64 μM of opsin) was thawed and vortexed thoroughly. A 200 μL aliquot of this sample was transferred into a 0.5 mL Eppendorf tube. To it was added 10 μL of 20 mM drug stock solution in EtOH, and the mixture vortexed for 1 min. The tube was incubated at 37° C. in a Thermo Scientific microprocessor controlled 280 series water bath for 3 min before 5 μL freshly prepared 2.4 mM RAL solution in EtOH was added (the nominal starting concentrations of drug and RAL are 1.00 mM and 60 μM, respectively). After vortexing for 1 min, the tube was incubated at 37° C. and aliquots of the reaction mixture (25 μL each) were taken periodically and added onto 10 mg of solid $NaBH_4$ in a 0.5 mL Eppendorf tube. To the latter was added 400 μL of 2:1 (v/v) EtOH/HOAc. The reduction mixture was vortexed for 1 min and centrifuged. The supernatant was separated, and analyzed by HPLC using a standard HPLC method:

Instrument: HPLC-PE-97
Column: Waters Sunfire $C_{18}$ 3.5 μm/4.6×100 mm column
Solvent A: 0.05% HCOOH/95% HPLC grade water/5% HPLC grade MeCN
Solvent B: 0.05% HCOOH HPLC grade MeCN
Pump program: 0-3 min 5-100% B, 3-30 min 100% B, 31-32 min 100%-5% B, 32-35 min 5% B Flow rate: 1 mL/min
Detector wavelengths: 329 and 250 nm
Reference wavelength: 400 nm
Injection volume: 50 μL.

The RAL depletion percentages were calculated by normalization of retinol (ROL) and RAL-drug peak integrals, which were then plotted against reaction time. Least squares fit of the RAL depletion plot according to pseudo-first order kinetics yielded observed first order rate constant $k_{obsd}$, and $k_{app}$ is calculated according to $k_{obsd}=k_{app}[drug]$. $K_{app}$ was calculated from the equilibrium concentrations of free RAL, free drug and RAL-drug according to equation (1). $\Delta G_{app}$ was calculated according to equation (2).

Preparation of the adducts RAL-1, RAL-2 and RAL-3 of RAL with Compounds 1, 2 and 3. Mixtures of 25.6 mg (0.09 mmol) RAL and 0.11 mmol of either Compound 1 or 2, or Compound 3 (2-[3-amino-6-chloroquinolin-2-yl]propan-2-ol, wherein the carbinol has no peri-interaction), in 1 mL dry benzene were stirred in the dark under argon at room temperature for 1 hr. The mixtures were evaporated to dryness and the residues evaporated twice from 2 mL benzene. The residues were dissolved in 1 mL benzene, allowed to stand 1 hr at room temperature and evaporated to dryness. The residues were evaporated from benzene (3×2 mL), redesolved in 0.5 mL dry benzene, and the solutions loaded on silica gel columns. The columns were first eluted with hexanes, and further eluted with 50:1 (v/v) hexanes-ethyl acetate. The fractions containing the adducts were evaporated to dryness to provide pure RAL-1, RAL-2 and RAL-3. The adducts were dissolved in 0.8 mL dry $CDCl_3$, and the ratio of imine and oxaminal tautomers were determined from their $^1H$ NMR spectra. The values of $K_T$ and $\Delta G_T$ were calculated according to equations (3) and (4). Both RAL-1 and RAL-2 exist exclusively as the oxaminal tautomers, while RAL-3 exists as a 1:1.3 mixture of both the imine and oxaminal forms, respectively.

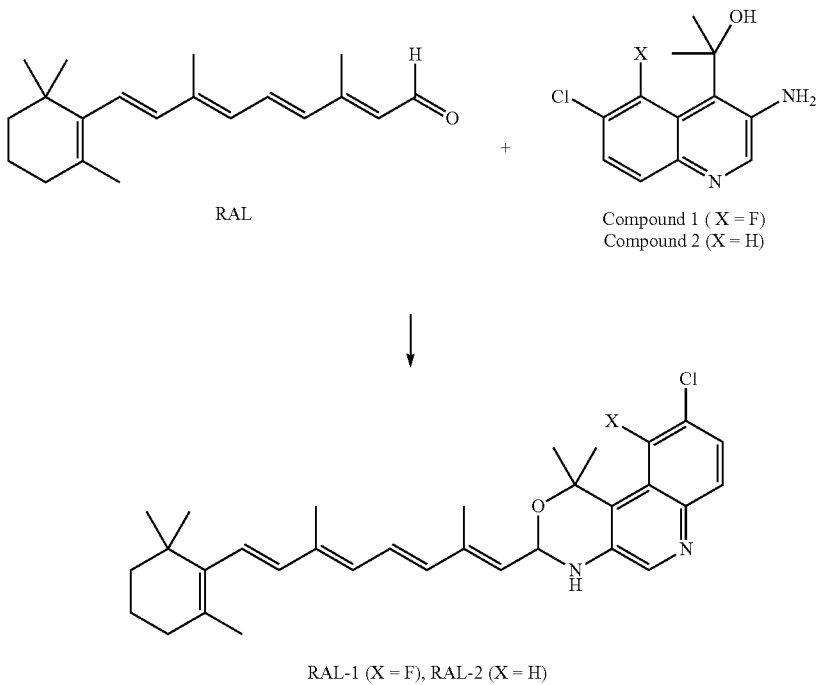

RAL

Compound 1 ( X = F )
Compound 2 (X = H)

RAL-1 (X = F), RAL-2 (X = H)

RAL-1: 9-chloro-3-((1E,3E,5E,7E)-2,6-dimethyl-8-(2,6,6-trimethylcyclohex-1-enyl)octa-1,3,5,7-tetraenyl)-10-fluoro-3,4-dihydro-1H-[1,3]oxazino[4,5-c]quinoline.

$^1H$ NMR (400 MHz, $CDCl_3$) RAL-1 δ: 1.04 (s, 6H), 1.47 (m, 2H), 1.62 (m, 2H), 1.722 (d, 3H, J=1.2 Hz), 1.725 (d, 3H, J=2.8 Hz), 1.9-2.1 (11H), 4.64 (br, 1H, NH), 5.06 (d, 1H, J=7.2 Hz), 5.61 (d, 1H, J=7.2 Hz), 6.13 (d, 1H, J=10.8 Hz), 6.14 (d, 1H, J=16.0 Hz), 6.20 (d, 1H, J=16.4 Hz), 6.31 (d, 1H, J=15.2 Hz), 6.74 (dd, 1H, J=11.6, 15.2 Hz), 7.44 (dd, 1H, J=7.2, 8.8 Hz), 7.76 (dd, 1H, J=1.6, 9.2 Hz), 8.36 (s, 1H).

$^{13}C$ NMR (100 MHz, $CDCl_3$) RAL-1 δ: 12.8, 13.6, 19.3, 21.7, 28.7 (d, $J_{C-F}$=16 Hz), 29.0, 29.2 (d, $J_{C-F}$=13 Hz), 33.1, 34.3, 39.6, 73.4, 76.8, 117.3 (d, $J_{C-F}$=23 Hz), 120.0 (d, $J_{C-F}$=22 Hz), 125.7 (d, $J_{C-F}$=4 Hz), 125.9, 126.96, 126.98, 127.4 (d, $J_{C-F}$=4 Hz), 127.5, 129.6, 129.7, 135.1, 135.9, 137.3, 137.4, 137.8, 140.4, 143.6 (d, $J_{C-F}$=4 Hz), 145.7, 151.2 (d, $J_{C-F}$=152 Hz).

RAL-2: 9-chloro-3-((1E,3E,5E,7E)-2,6-dimethyl-8-(2,6,6-trimethylcyclohex-1-enyl)octa-1,3,5,7-tetraenyl)-3,4-dihydro-1H-[1,3]oxazino[4,5-c]quinoline.

$^1$H NMR (400 MHz, CDCl$_3$) RAL-2 δ: 1.03 (s, 6H), 1.47 (m, 2H), 1.62 (m, 2H), 1.72 (s, 3H), 1.80 (s, 3H), 1.96 (s, 3H), 1.98 (s, 3H), 2.01 (s, 3H), 2.02 (t, 2H, J=7.2 Hz), 4.50 (br, 1H, NH), 5.53 (dd, 1H, J=4.4, 6.8 Hz), 5.62 (d, 1H, J=7.2 Hz), 6.13 (d, 1H, J=11.2 Hz), 6.14 (d, 1H, J=16.0 Hz), 6.20 (d, 1H, J=16.4 Hz), 6.31 (d, 1H, J=15.2 Hz), 6.73 (dd, 1H, J=11.2, 15.2 Hz), 7.40 (dd, 1H, J=2.0, 8.8 Hz), 7.84 (d, 1H, J=2.0 Hz), 7.92 (d, 1H, J=8.8 Hz), 8.39 (s, 1H).

$^{13}$C NMR (100 MHz, CDCl$_3$) RAL-2 δ: 13.0, 13.7, 19.4, 21.9, 28.8, 29.1, 29.4, 33.3, 34.4, 39.8, 74.5, 75.4, 123.2, 126.0, 126.3, 127.0, 127.1, 127.6, 128.5, 129.7, 129.9, 132.3, 132.6, 135.3, 135.6, 137.5, 137.6, 137.9, 140.5, 142.4, 144.9.

RAL-3: exists as a 1:1.3 mixture of imine and oxaminal tautomers.

RAL-3 imine tautomer (im)

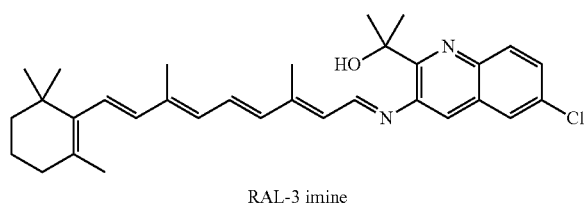 [SMILES: CC1=C(/C=C/C(C)=C/C=C/C(C)=C/C=N/c2cc3cc(Cl)ccc3nc2C(C)(C)O)C(C)(C)CCC1]

RAL-3 imine 2-(6-chloro-3-((E)-2E,4E,6E,8E)-3,7-dimethyl-9-(2,6,6-trimethylcyclohex-1-enyl)nona-2,4,6,8-tetraenylidene)amino)quinolin-2-yl)propan-2-ol.

RAL-3 oxaminal tautomer (ox)

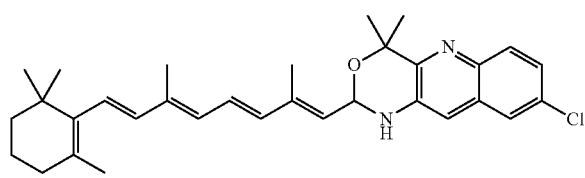

RAL-3 oxaminal 9-chloro-3-((1E,3E,5E,7E)-2,6-dimethyl-8-(2,6,6-trimethyl-cyclohex-1-enyl)octa-1,3,5,7-tetraenyl)-3,4-dihydro-1H-[1,3]oxazino[4,5-c]quinoline.

$^1$H NMR (400 MHz, CDCl$_3$) δ: 1.04 (s, 3.4H, ox), 1.05 (s, 2.6H, im), 1.49 (m, 2H, im and ox), 1.63 (m, 2H, im and ox), 1.69 (s, 3.4H, ox), 1.72 (s, 1.7H, ox), 1.74 (s, 2.6H, im), 1.77 (s, 1.6H, im), 1.98 (s, 1.6H, im), 2.01 (s, 1.7H, ox), 2.03 (br, 2H, im and ox), 2.04 (s, 1.7H, ox), 2.26 (s, 1.3H, im), 4.48 (br, 0.4H, OH, im), 5.61 (d, 0.6H, J=6.8 Hz, ox), 5.70 (d, 0.57H, J=6.8 Hz, ox), 6.11-6.32 (3.5H, im and ox), 6.49 (d, 0.4H, J=14.8 Hz, im), 6.51 (d, 0.4H, J=8.4 Hz, im), 6.65 (br, 0.6H, NH, ox), 6.72 (dd, 0.4H, J=11.2, 14.8 Hz, im), 7.03 (dd, 0.6H, J=11.2, 15.2 Hz, ox), 7.04 (s, 0.6H, ox), 7.35 (dd, 0.6H, J=2.0, 8.8 Hz, ox), 7.46 (s, 0.4H, im), 7.55 (d, 0.6H, J=2.0 Hz, ox), 7.58 (dd, 0.4H, J=2.0, 8.8 Hz, im), 7.76 (d, 0.4H, J=2.0 Hz, im), 7.83 (d, 0.6H, J=8.8 Hz, ox), 7.97 (d, 0.4H, J=8.8 Hz, im), 8.53 (d, 0.4H, J=9.6 Hz, im).

TABLE 1

In vitro drug evaluation data summary for reaction of drug compounds with RAL

| drug | $k_{app}^a$ (M$^{-1}$·h$^{-1}$)$^a$ | $K_{app}^b$ | $\Delta G_{app}$ (kcal/mol)$^c$ | $K_T^d$ | $\Delta G_T$ (kcal/mol)$^e$ |
|---|---|---|---|---|---|
| Compound 1 | 3080 | >2 × 10$^7$ | <−10 | >>1000 | <<−4 |
| Compound 2 | 1900 | >2 × 10$^7$ | <−10 | >>1000 | <<−4 |
| Compound 3 | 3570 | 1.55 × 10$^5$ | −7.4 | 1.3 | −0.155 |

$^a$Apparent second order rate constant of RAL depletion by drug compounds in rod outer segment preparation containing 64 μM opsin at 37° C.
$^b$Apparent equilibrium constant of RAL depletion by drug compounds in rod outer segment prep containing 64 μM opsin at 37° C.
$^c$Apparent free energy change of RAL depletion by drug compounds in rod outer segment preparation containing 64 μM opsin at 37° C.
$^d$Equilibrium constant of tautomerism from imine to oxaminal (ring closed) in CDCl$_3$ at 25° C.
$^e$Free energy change of tautomerism from imine to oxaminal (ring closed) in CDCl$_3$ at 25° C.

Example 4

Pharmaceutical Formulations

As a specific embodiment of an oral composition of a compound of the present invention, 50 mg of the milled compound of any of the compounds of the invention is formulated with sufficient finely divided lactose to provide a total amount of 580 to 590 mg to fill a size O hard gelatin capsule.

As a second specific embodiment of an oral pharmaceutical composition, a 100 mg potency tablet is composed of 100 mg of any one of the compounds of the invention, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

As a specific embodiment of a topical ocular composition, approximately 60% of the targeted weight of sterile water is added to a 1 L beaker. Stirring is adjusted so as not to incorporate air. Anhydrous dibasic sodium phosphate (0.83% of the total batch weight) and sodium phosphate monobasic monohydrate (0.017% of the total batch weight) is added to the vessel and mixed until dissolved. β-cyclodextrin sulfobutylether (9.5% of the total batch weight) is slowly added to the beaker and the solution mixed until dissolved. Any one of the compounds of the invention (0.1% of the total batch weight) is slowly added and mixed until dissolved. A sample is extracted and the pH measured. If the pH is not in the range 7.3±0.05, adjustment is made with 1N NaOH or 1N HCl. The batch weight is measured and the amount of sterile water needed to bring to final batch weight is determined and added. The solution is then sterilized by ultrafiltration.

EQUIVALENTS

Those skilled in the art will recognize, or be able to ascertain using no more than routine experimentation, many equivalents to the specific embodiments and methods described herein. Such equivalents are intended to be encompassed by the scope of the present invention.

All patents, patent applications, and literature references cited herein are hereby expressly incorporated by reference.

The invention claimed is:

1. A compound of formula (I):

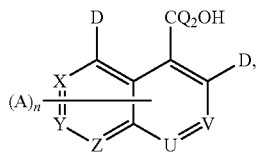
(I)

or a pharmaceutically acceptable salt thereof, wherein:
each D is independently H, $NH_2$ or A, wherein one D is $NH_2$ and the other D is H or A;
U, V, Z, Y and X are each independently CH, CA or N, wherein one of U, V, Z, Y and X is N and the other of U, V, Z, Y and X is CH or CA;
each A is independently selected from F, Cl, and Br,
each Q is independently straight chain $C_{1-6}$-alkyl or branched chain $C_{3-6}$-alkyl, wherein the alkyl is optionally substituted with 1-6 F, or
both Q, together with the carbon atom to which they are attached, form a $C_{3-6}$-carbocycle or a saturated heterocycle selected from

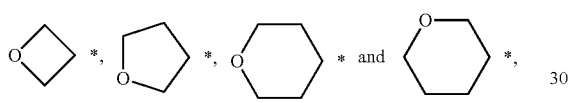

wherein "*" denotes the position of the carbon atom to which both Q are attached, wherein the carbocycle or the heterocycle is optionally substituted with one or more $R_Q$, wherein each $R_Q$ is independently H, straight chain $C_{1-6}$-alkyl, branched chain $C_{3-6}$-alkyl or halogen; and
n is 0, 1, 2, or 3.

2. The compound of claim 1, wherein one D is $NH_2$ and the other D is H, F or Cl.

3. The compound of claim 1, wherein U is N.

4. The compound of claim 1, wherein Y is N.

5. The compound of claim 1, wherein n is 0, 1 or 2.

6. The compound of claim 1, wherein each A is independently F or Cl.

7. The compound of claim 5, wherein at least one Q is straight chain $C_{1-6}$-alkyl.

8. The compound of claim 7, wherein at least one Q is methyl, ethyl or propyl.

9. The compound of claim 8, wherein each Q is methyl.

10. The compound of claim 1, wherein at least one Q is straight chain $C_{1-6}$-alkyl substituted with 1-6 F.

11. The compound of claim 10, wherein at least one Q is methyl, ethyl or propyl substituted with 1-6 F.

12. The compound of claim 11, wherein at least one Q is $CH_2F$, $CHF_2$, or $CF_3$.

13. The compound of claim 1, wherein both Q, together with the carbon atom to which they are attached, form a ring selected from

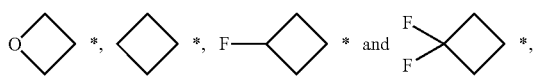

wherein "*" denotes the position of the carbon atom to which both Q are attached.

14. The compound of claim 1, selected from the group consisting of:

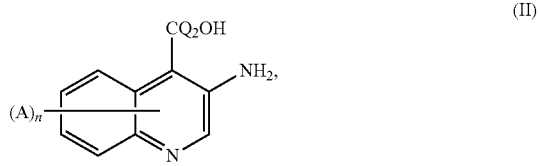
(II)

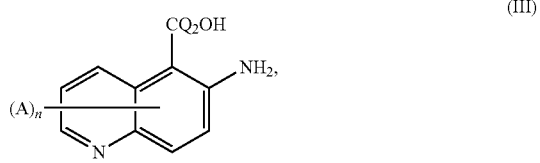
(III)

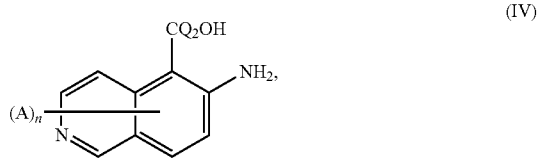
(IV)

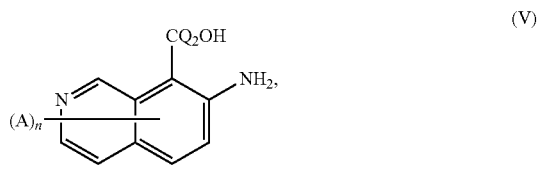
(V)

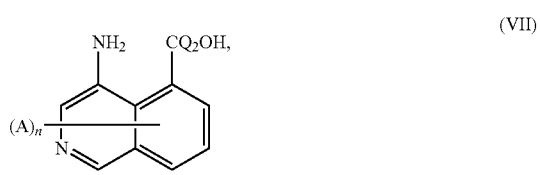
(VII)

and a pharmaceutically acceptable salt thereof.

15. The compound of claim 14, wherein n is 0, 1 or 2.

16. The compound of claim 15, selected from the group consisting of:

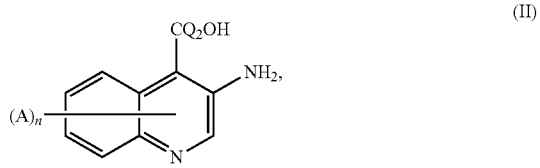
(II)

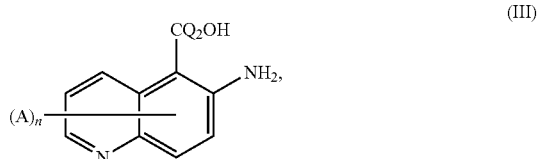
(III)

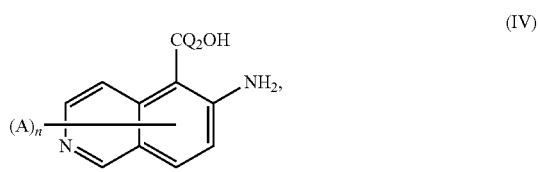
(IV)

and a pharmaceutically acceptable salt thereof.

17. The compound of claim 16, which is or a pharmaceutically acceptable salt thereof.

18. The compound of claim 17, wherein each A is independently F or Cl.

19. The compound of claim 18, wherein each Q is independently selected from straight chain $C_{1-6}$ alkyl or branched $C_{3-6}$ alkyl.

20. The compound of claim 18, wherein both Q, together with the carbon atom to which they are attached, form a ring selected from wherein "*" denotes the position of the carbon atom to which both Q are attached.

21. The compound of claim 17, selected from the group consisting of:

and a pharmaceutically acceptable salt thereof.

22. The compound of claim 21, selected from the group consisting of:

and a pharmaceutically acceptable salt thereof.

23. The compound of claim 14, which is

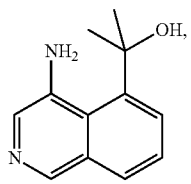

or a pharmaceutically acceptable salt thereof.

24. A pharmaceutical composition comprising a compound of claim 1 or a pharmaceutically acceptable salt thereof and a pharmaceutically acceptable carrier.

25. The pharmaceutical composition of claim 24, wherein the compound is selected from the group consisting of:

(a)
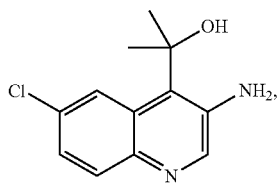

(b)
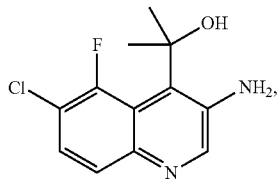

(c)
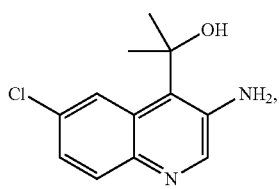

(d)
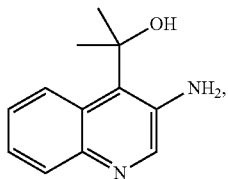

(e)
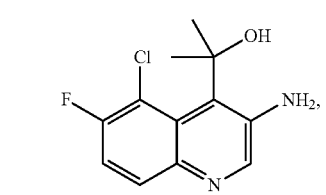

(f)
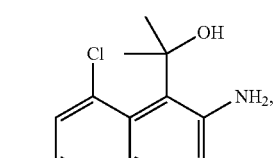

(g)
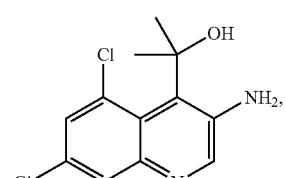

(h)
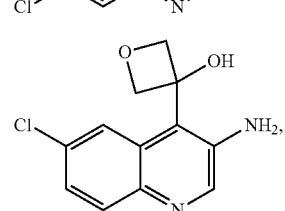

(i)
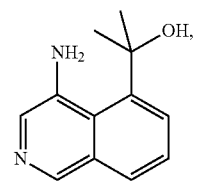

and a pharmaceutically acceptable salt thereof.

26. A method of treating macular degeneration or a retinal disease or disorder characterized by accumulation of A2E and/or lipofuscin in a subject, comprising administering to the subject in need thereof a therapeutically effective amount of a pharmaceutical composition comprising a compound of of formula (I):

(I)

or a pharmaceutically acceptable salt thereof, wherein:
each D is independently H, NH$_2$ or A, wherein one D is NH$_2$ and the other D is H or A;
U, V, Z, Y and X are each independently CH, CA or N, wherein one of U, V, Z, Y and X is N and the other of U, V, Z, Y and X is CH or CA;
each A is independently selected from F, Cl, Br, CF$_2$H, CF$_3$, R', OR, COOR, CON(R)$_2$, N(R')$_2$, NRCOR, NRCOOR', NRCON(R)$_2$, NRSO$_2$R', SO$_2$R', SO$_2$N(R)$_2$, unsubstituted phenyl, and phenyl substituted with 1-3 substituents, wherein each substituent is independently selected from F, Cl, $CF_2H$, $CF_3$, OR and R', or two such substituents, together with the carbon atoms of the phenyl ring to which they are attached, form a five- or six-membered ring having a structure selected from

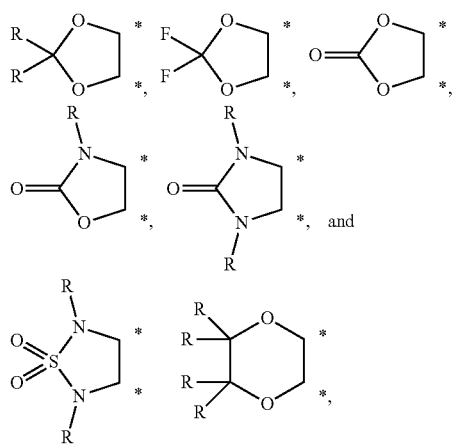

wherein "*" denotes the positions of the carbon atoms to which the substituents are attached on the phenyl ring,
alternatively, when attached to adjacent atoms in formula (I), any two A, together with the atoms to which they are attached, form a five- or six-membered ring having a structure selected from

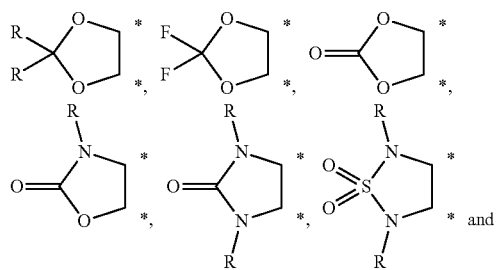

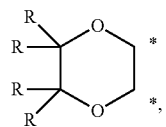

wherein "*" denotes the positions of the atoms to which the two A are attached on formula (I);

each R is independently H, straight $C_{1-6}$-alkyl, branched chain $C_{3-6}$-alkyl or cyclic $C_{3-6}$-alkyl;

each R' is independently straight $C_{1-6}$-alkyl, branched chain $C_{3-6}$-alkyl or cyclic $C_{3-6}$-alkyl;

each $R_Q$ is independently H, straight $C_{1-6}$-alkyl, branched chain $C_{3-6}$-alkyl or halogen;

each Q is independently H, straight $C_{1-6}$-alkyl or branched chain $C_{3-6}$-alkyl, wherein the alkyl is optionally substituted with 1-6 F, or both Q, together with the carbon atom to which they are attached, form a $C_{3-6}$-carbocycle or a saturated heterocycle selected from

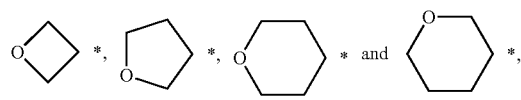

wherein "*" denotes the position of the carbon atom to which both Q are attached, wherein the carbocycle or the heterocycle is optionally substituted with one or more $R_Q$; and n is 0, 1, 2, or 3.

27. The method of claim 26, wherein the macular degeneration is age related macular degeneration (AMD).

28. The method of claim 27, wherein the AMD is dry AMD or wet AMD.

29. The method of claim 26, wherein the macular degeneration is Stargardt's disease.

* * * * *